US008540980B2

(12) United States Patent
London et al.

(10) Patent No.: US 8,540,980 B2
(45) Date of Patent: *Sep. 24, 2013

(54) DELIVERY SYSTEM FOR BIOLOGICAL COMPONENT

(71) Applicant: TNTGamble, Inc., Redmond, WA (US)

(72) Inventors: Christopher London, Redmond, WA (US); Stephen J. Turner, Snoqualmie, WA (US); Tanya Borek, Bellevue, WA (US); Catherine Federici, Seattle, WA (US); Michael P. Hite, Normandy Park, WA (US)

(73) Assignee: TNTGamble, Inc., Redmond, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/686,147

(22) Filed: Nov. 27, 2012

(65) Prior Publication Data

US 2013/0084265 A1 Apr. 4, 2013

Related U.S. Application Data

(63) Continuation of application No. 11/634,397, filed on Dec. 5, 2006, now abandoned, which is a continuation-in-part of application No. 10/261,639, filed on Sep. 30, 2002, now Pat. No. 8,007,777.

(60) Provisional application No. 60/325,937, filed on Sep. 28, 2001.

(51) Int. Cl.
*A01N 63/00* (2006.01)

(52) U.S. Cl.
USPC ...... 424/93.45; 424/93.1; 424/93.4; 424/464; 424/93.46; 424/93.5; 424/93.51; 435/252.1; 435/252.9

(58) Field of Classification Search
USPC .............. 424/93.1, 93.45, 93.4, 464, 93.46, 424/93.5, 93.51; 435/252.1, 252.9
See application file for complete search history.

(56) References Cited

U.S. PATENT DOCUMENTS

| | | |
|---|---|---|
| 3,065,142 A | 11/1962 | Antonides et al. |
| 3,072,528 A | 1/1963 | Kludas |
| 4,264,573 A | 4/1981 | Powell et al. |
| 4,542,020 A | 9/1985 | Jackson et al. |
| 4,699,793 A | 10/1987 | Eguchi et al. |
| 4,755,180 A | 7/1988 | Ayer et al. |
| 4,777,033 A | 10/1988 | Ikura et al. |
| 4,806,368 A | 2/1989 | Reddy |
| 4,956,295 A | 9/1990 | Sudoma |
| 4,966,768 A | 10/1990 | Michelucci et al. |
| 5,147,668 A | 9/1992 | Munk |
| 5,194,172 A | 3/1993 | Taneri |
| 5,213,808 A | 5/1993 | Bar-Shalom et al. |
| 5,288,507 A | 2/1994 | Sims et al. |
| 5,419,917 A | 5/1995 | Chen et al. |
| 5,503,750 A | 4/1996 | Russo, Jr. et al. |
| 5,531,681 A | 7/1996 | Walton et al. |
| 5,789,446 A | 8/1998 | Uchiyama et al. |
| 5,830,884 A | 11/1998 | Kassica |
| 6,090,411 A | 7/2000 | Pillay et al. |
| 6,127,561 A | 10/2000 | Jeromin |
| 6,241,983 B1 | 6/2001 | Paul et al. |
| 6,306,896 B1 | 10/2001 | Scheiwe |
| 6,337,091 B1 | 1/2002 | Kim et al. |
| 6,365,148 B1 | 4/2002 | Kim et al. |
| 6,375,994 B1 | 4/2002 | Paul |
| 6,399,594 B2 | 6/2002 | De Haan et al. |
| 6,403,120 B1 | 6/2002 | Sherman et al. |
| 6,413,494 B1 | 7/2002 | Lee et al. |
| 6,458,384 B2 | 10/2002 | Jaenicke et al. |
| 6,479,051 B1 | 11/2002 | Bruce |
| 6,517,868 B2 | 2/2003 | Fassihi et al. |
| 6,716,449 B2 | 4/2004 | Oshlack et al. |
| 6,777,000 B2 | 8/2004 | Ni et al. |
| 6,812,351 B2 | 11/2004 | Weiguny et al. |
| 6,936,275 B2 | 8/2005 | Fassihi et al. |
| 7,122,370 B2 | 10/2006 | Poribcan |
| 7,201,923 B1 | 4/2007 | van Lengerich |
| 7,229,642 B2 | 6/2007 | Fassihi et al. |
| 7,498,310 B1 | 3/2009 | Schonrock et al. |
| 8,007,777 B2 * | 8/2011 | Borek et al. ................ 424/93.1 |
| 2002/0015756 A1 * | 2/2002 | Gutkevich ..................... 426/34 |
| 2002/0107495 A1 | 8/2002 | Chen et al. |
| 2003/0021841 A1 | 1/2003 | Matharu et al. |
| 2011/0232736 A1 | 9/2011 | Goldstein et al. |

FOREIGN PATENT DOCUMENTS

| | | |
|---|---|---|
| EP | 0427519 | 5/1991 |
| EP | 1072258 | 1/2001 |
| JP | 09-110705 | 4/1997 |
| RU | 2118535 | 9/1998 |

(Continued)

OTHER PUBLICATIONS

Chen et al., "Chemical, Physical, and Baking Properties of Apple Fiber Compared with Wheat and Oat Bran," Cereal Chemistry, vol. 65, No. 3: pp. 244-247, 1988.

Maggi et al., "Technological and biological evaluaton of tablets containing different strains of *Lactobacilli* for vaginal administration." Eu. J. Pharm Biopharm., vol. 50, No. 3: pp. 389-395, 2000.

Pillay et al., "A novel approach for constant rate delivery of highly soluble bioactives from a simple monolithic system." J. Controlled Release, vol. 67: pp. 67-78, 2000.

Quadir et al., "Evaluation of Hydrophobic Materials as Matrices for Controlled-Release Drug Delivery." Pakistan Journal of Pharmaceutical Science, vol. 16, No. 2: pp. 17-28, 2003.

Raffalt et al., "Tablet Formulations Containing Viable Lactic Acid Bacteria as Active Ingredient." Proceedings for the international symposium on controlled release bioactive materials. No. 26: pp. 865-866, 1999.

(Continued)

*Primary Examiner* — Susan Hanley
(74) *Attorney, Agent, or Firm* — Miller Nash LLP

(57) ABSTRACT

A controlled release delivery system composition and method applied to humans and animals, for oral, anal or vaginal administration of a biological component is disclosed. Preferably, a bacterium is delivered, and more preferably the bacterium is probiotic in nature, however, the biological component is not limited to the bacterium.

18 Claims, 13 Drawing Sheets

(56) References Cited

FOREIGN PATENT DOCUMENTS

| | | |
|---|---|---|
| WO | WO 91/07949 | 6/1991 |
| WO | WO 97/48386 | 12/1997 |
| WO | WO 98/08529 | 3/1998 |
| WO | WO 99/52507 | 10/1999 |
| WO | WO 02/094424 | 11/2002 |

OTHER PUBLICATIONS

Schilling et al., "Properties of melt extruded enteric matrix pellets." European J Pharma. Biopharma, vol. 74: pp. 352-361, 2010.

curehunter.com/public/keywordSummaryCO09683-witepsol.do, downloaded May 7, 2010.

www.treetopingredients.com/applefiber.asp (1 of 3) downloaded Nov. 10, 2010.

Webster's II New Riverside University Dictionary (1997) (Houghton-Mifflin: Boston, MA) p. 1175.

The freedictionary.com definition of monolithic downloaded Jun. 18, 2012.

\* cited by examiner

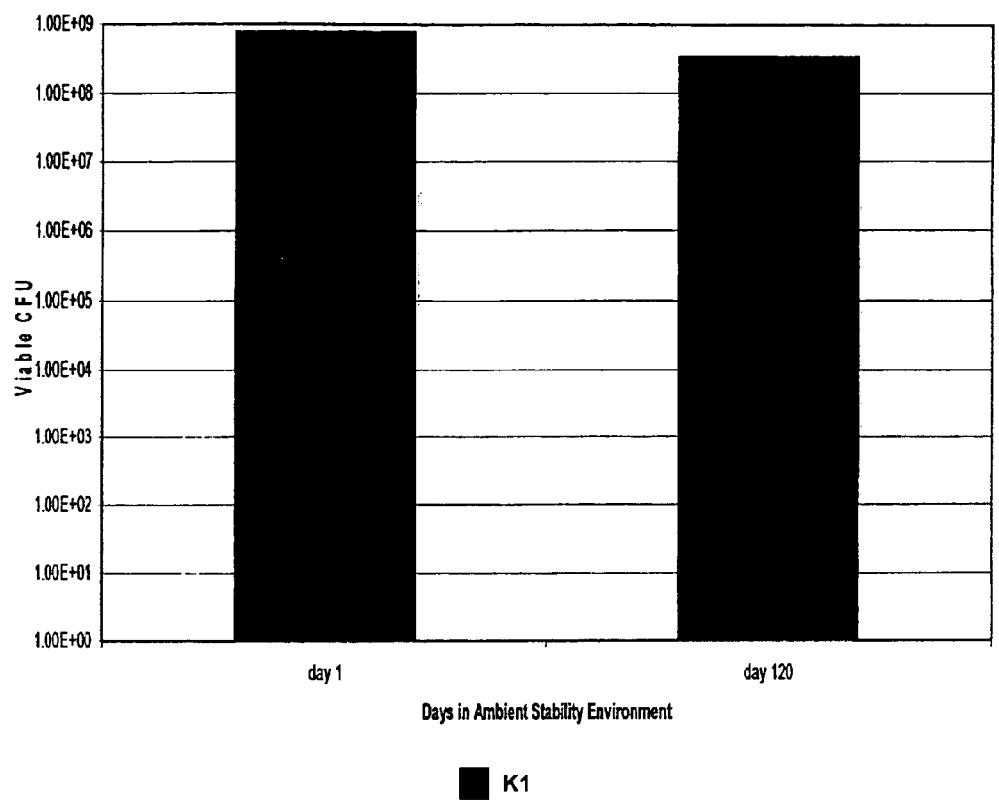

DELIVERY SYSTEM FOR BIOLOGICAL COMPONENT

CROSS-REFERENCE(S) TO RELATED APPLICATION(S)

The present application is a continuation of U.S. patent application Ser. No. 11/634,397 now U.S. Pat. No. 8,007,777, filed Dec. 5, 2006, which is a continuation-in-part of U.S. patent application Ser. No. 10/261,639, filed Sep. 30, 2002, which claims priority to U.S. provisional patent application Ser. No. 60/325,937, filed Sep. 28, 2001. The disclosure of these applications is hereby expressly incorporated herein by reference in their entirety.

BACKGROUND

The present invention is directed to a controlled release solid dosage form for biological components (BC). In addition, the invention is directed to a method of delivery of BCs over an extended timeframe.

As a biological substance passes through the gastrointestinal (GI) tract of humans or animals, it is subjected to a wide range of pH values ranging from the neutral pH of the mouth, to the acidic conditions of the stomach, and to the different conditions of the intestinal tract. The GI tract has significantly different conditions in the gastric portion, the stomach, as compared to the intestinal tract, the small and large intestines, due to different pH ranges. Because the majority of biologically active components are highly pH sensitive, these changes in pH can cause significant effects upon the stability of the BCs and their ability to function in vivo. For example, many proteins included in BCs denature in acidic environments. Once BC proteins are denatured, their biological activity, if still present, significantly differs from the non-denatured state. For a BC to be functional, it must survive the GI tract with minimal exposure to pH fluctuations. Further, BCs are also extremely sensitive to enzymes bringing about enzymatic degradation. For example, one barrier to the oral administration of insulin is its susceptibility to enzymatic degradation.

The oral administration of BCs without a controlled release delivery system has as a significant disadvantage not allowing the BC to bypass the low-pH and enzyme-rich environment of the stomach, thereby potentially decreasing the viability of the BC. For those devices which employ an enteric coating mechanism to survive the gastric environment, the shortcomings may be two-fold. First, the process of coating the dosage form or its contents with an enteric coating mechanism may result in significantly lowered viability of the BC. Second, the downfall of merely by-passing the stomach is the explosive delivery of the BC immediately upon exiting the stomach. This non-specific delivery is ineffectual and primitive in view of certain delivery needs of BCs because the bioavailability of BCs is often site dependent. Therefore, the enteric coating process typically used in the pharmaceutical industry is not used in this invention.

BCs may be targeted either through modification of the BC itself or through the controlled release of the BC within a desired physiologic window. One such BC that displays such site-specificity is the lactic acid bacteria, *Lactobacillus Acidophilus*, also referred to as a probiotic. Probiotic bacteria promote intestinal health by assisting the naturally occurring flora within the GI tract to reestablish themselves. Probiotics are also useful after antiobiotic therapy. *L. Acidophilus* is one example of other probiotics, including *Lactobacillus bulgaricus, Lactobacillus casei* subsp. *Rhamnosus, Lactobacillus casei* subsp. *Casei, Lactobacillus salivarius, Lactobacillus brevis, Lactobacillus reuteri, Lactococcus lactis* subsp. *Lactis, Enterococcus faecium, Lactobacillus plantarum, Streptococcus thermophilus, Bifidobacterium infantis, Bifidobacterium Bifidum, Bifidobacterium longum, Saccharomyces boulardii*, and various modified soil organisms.

Various strains of probiotic organisms will attach at a different locations of the intestinal tract, preferentially attaching within a region either slightly proximal or distal to other probiotic strains of the same, or nearly the same genus. These preferential regions of attachment are of particular importance relative to employing the probiotic as delivery systems for genomic or proteomic therapy, whether directly or as carriers for other vectors containing genetic or proteomic BCs.

Beneficial microorganisms, for example, but not limited to, gastrointestinal flora such as lactic acid bacteria and yeast are an essential constituent of metabolism and immune response. Supplementation of beneficial microorganisms is a valid mechanism for replacement of flora lost due to antibiotic treatment, enhancement of naturally-occurring levels of beneficial flora, enhancing competitive inhibition and otherwise preventing enteropathogens, and altering the metabolism of ingested substances. Probiotics are one example of beneficial microorganisms.

Solid oral dosage forms employing controlled release have been increasingly demonstrated to be beneficial to the administration of pharmaceutical compounds, enhancing safety and consumer compliance, minimizing side effects and providing new therapeutic benefits. The four generalized platforms for controlled release solid oral dosage forms are diffusion, reservoir, pore-forming wax, or coated-bead systems. These platforms for controlled release have generally not been applied to BCs, however, due to high development costs, bioavailability issues, and internal instability of the BC within the dosage form. Where these platforms have been applied to BCs, the applications have not resulted in controlled release of the BCs. In the past, enteric coating technologies and other mechanisms of delayed release have been limited to features with explosive delivery after the stomach rather than controlled release and delivery of the BCs.

Controlled release delivery systems can take many forms including polymeric matrix systems, wax matrix systems, multi-particulate systems, and combinations thereof. The most commonly used delivery systems can be broadly classified as diffusion, reservoir, pore-forming wax, or coated-bead systems. Diffusion devices are composed of a drug dispensed in a polymer which diffuses from the entire physical tablet. Reservoir devices usually consist of a semi-permeable barrier which is involved in the release of the active ingredient from a core site within the tablet. Coated-bead systems employ a pH-sensitive or enteric coating of aggregated particles of the active ingredient packaged in capsule form. Pore-forming wax systems incorporate the active ingredient into a wax base and rely upon the rate of diffusion to control the release of the active ingredient.

In tableted, pore forming wax matrices, the BC and a water-soluble polymer are introduced into a wax or wax-like compound such as paraffin or guar gum, and then placed in an aqueous environment so as to allow the water-soluble polymer to dissolve out of the wax, resulting in the formation of pores. Upon contact with the GI fluid, the pores facilitate diffusion-mediated release of the BC. The rate of release of the BC is dependent upon non-linear erosion.

Coated-bead systems are one of the few delivery systems available in both tablet and capsule forms. The BC is encased within a bead using one of the varieties of processes available, such as spheronization-extrusion or coating of non-pareils. The coated BC is then further coated with an enteric coating or employed in a blend of coated beads with differing release rates for extended release formulations. The BC may also be blended or granulated with polymers before enteric coating to provide an additional level of control. The coated beads themselves may also be combined with polymers to create a hybrid diffusion or wax-based system. Coated-bead systems are complex to manufacture, requiring large numbers of excipients, use of solvents, and long manufacturing time. The use of such solvents and the manufacturing processes required to apply such solvents may expose the BC to adverse environmental conditions and cause a loss of the viability of the BC. This is especially concerning in the case of lyophilized BCs, where any exposure to moisture may cause significant reduction in viability.

An example of a reservoir system is the push-pull osmotic pump. These osmotically-controlled delivery systems feature a bi-layer tablet coated with a semi-permeable membrane, possessing a laser-bored orifice through which the BC is pushed as aqueous solution is absorbed into the tablet. There are a number of osmotic delivery systems on the market that work via a similar physical principle; these osmotic systems produce very replicable, linear release. Manufacturing this osmotic delivery system is definitively non-conventional, requiring specialized equipment and additional processing steps. The inherent complexity of the design adds corresponding complexity to the development and scale-up of any osmotic membrane product.

The diffusion tablet systems rely on hydrophilic polymer swelling for control of BC release. These polymer systems can be sub-classified as conventional hydrogel systems and modified polymer systems. Conventional hydrogel systems rely upon the penetration of water to form a gel-like phase through which the bioactive agent is released. These hydrogel systems often incorporate the BC in a single polymer such as polyethylene oxide or hydroxypropyl methylcellulose. In the case of the modified polymer systems, polymers with differing physical characteristics—such as one that is hydrophilic (e.g. HPMC), and one that is pH-dependent in its swelling characteristics (e.g. pectin), are combined with the BC. When these polymers interact with dissolution media, a transition phase or interfacial front develops, forming a gradually dissociating semi-solid core surrounded by a gel periphery that allows the BC to be increasingly released as the matrix hydrates. The movement of the dosage form through the GI tract, through regions of increasing pH, permits further swelling and erosion of the matrix, culminating in a complete release of the BC and complete dissolution of the dosage form.

Prior art formulations cannot deliver beneficial microorganisms as part of BCs over an extended time period or to targeted individual regions of the GI tract. Prior art formulations require coating processes such as enteric coating to achieve gastric or stomach bypass. Further, prior art formulations fail to provide mechanisms for pH control thereby rendering pH sensitive strains much less viable due to variations in the pH of the GI tract. Further, prior art formulations lack mechanisms for isolating the BC from enzymatic degradation. Prior art formulations lack mechanisms to increase the stability of the dosage form itself through sequestration of available water. Prior art formulations utilizing dietary fiber as a carrier require too large a volume for efficient oral dosage form manufacture. These and other limitations and problems of the past are solved by the present invention.

SUMMARY

The present invention provides controlled release delivery systems for oral administration of a biological component. The invention can be used to administer BCs to humans or animals.

One embodiment of a controlled delivery system includes a hydrogel or modified matrix formed from an excipient of one or more hydrophilic polymers, polysaccharides, galactomannan gums, resins, polyethylene derivatives or hydrolyzed proteins, either alone or in combination, in which BCs are disposed. The BCs could include beneficial microorganisms, lyophilized bacteria and their associated lyophilized carrier proteins, vitamin B complex, vitamin C, other vitamins, nicotinic acid, glucosamine, chondroitin sulfate, caffeine, green tea, soy isoflavones, cranberry, echinacea, other herbals, St. johns wort, alpha lipoic acid, L. carnitine, pancreatic enzymes, hormones, other enzymes or other biologics. Optionally, the controlled delivery system includes one or more additional release modifying agents (as used herein, the terms "release modifying excipients" and "release modifying agents" are used interchangeably) with pH-specific or enzyme specific agents from the same group of hydrophilic agents for the purpose of attenuating the release of the lyophilized ingredients or other BCs. One or more physiologically acceptable eletrolytic agents or electrolytes, included for the purpose of pH control or available water-sequestration, may be optionally included in the controlled delivery system.

In another embodiment, the controlled delivery system includes a wax matrix composed of one or more inert insoluble waxes, polymers and/or inert fillers, alone or in combination, in which are disposed pore forming excipients and BCs, in one aspect comprising lyophilized bacteria and their associated lyophilized carrier proteins and in another aspect comprising vitamin B complex, vitamin C, other vitamins, nicotinic acid, glucosamine, chondroitin sulfate, caffeine, green tea, soy isoflavones, cranberry, echinacea, other herbals, St. johns wort, alpha lipoic acid, L. carnitine, pancreatic enzymes, hormones, other enzymes or other biologics.

Yet another embodiment of a controlled delivery system includes a multi-particulate system in which a plurality of granules, coated beads or coated non-pareils are distributed within the dosage form in either a simple or a modified polymer matrix or for the purposes of controlled release of beneficial microorganisms or other BCs in one aspect and in another aspect comprising lyophilized bacteria and their associated lyophilized carrier proteins.

In another embodiment, the invention constitutes a method for making an extended release dosage form, such as a tablet or capsule, from a pre-blend by mixing a beneficial microorganism with one or more polymers, gums, resins, polyethylene derivatives, or hydrolyzed proteins for the purpose of controlled release. Optionally, physiologically acceptable eletrolytic agents or electrolytes can be added to the controlled delivery system for the purpose of regulating internal pH within the dosage form or available for water-sequestration.

In another embodiment of the method of making an extended release dosage form, such as a tablet or capsule, the method includes mixing a beneficial microorganism with a pre-blend of one or more controlling excipients, fillers, desiccants, and flow agents that has been mechanically, chemically, or otherwise dried to reduce the available water present for the purpose of preventing undesirable interactions of the beneficial organisms and hydrophilic agents with any available water within the dosage form.

The controlled delivery system generally includes a hydrophilic agent, an electrolytic agent, and a BC and may optionally include fillers, release modifying agents, desiccants, and flow agents.

In one embodiment, a delivery system is disclosed including a hydrophilic or hydrophobic agent and a BC.

In another embodiment, a delivery system is disclosed including a hydrophilic agent, an electrolytic agent, and a BC.

In yet another embodiment, a delivery system is disclosed including a hydrophilic agent, a release modifying agent, and a BC.

In yet a further embodiment, a delivery system is disclosed including a hydrophobic agent, a release-modifying agent, and a BC.

In yet a further embodiment, a delivery system is disclosed including a hydrophilic agent, a release-modifying agent, and a BC.

In yet a further embodiment, a delivery system is disclosed including a hydrophilic agent, an electrolytic agent, and a BC.

In yet a further embodiment, a delivery system is disclosed including a hydrophobic agent, a release-modifying agent, an electrolytic agent, and a BC.

In yet a further embodiment, a delivery system is disclosed including a hydrophilic agent, release-modifying agent, electrolyte, and a BC.

The controlled release formulations or dosage forms for beneficial microorganisms have many advantages over the current art. Targeted delivery of beneficial microorganisms, such as probiotic bacteria, allows for dispersion of probiotic bacteria within regions of optimal attachment that may be specific to a given strain or therapeutic goal. One advantage is achieving gastric or stomach bypass for the BCs. Another advantage of the controlled release delivery system disclosed is the maintenance of a constant internal pH within the dosage form surrounding the BCs, in this case, beneficial microorganisms, allowing an optimal microenvironment for reconstitution of lyophilized ingredients to be created. This constant internal pH maximizes viability of the lyophilized ingredients to be released into the GI tract. Another advantage of the controlled delivery system disclosed is the inclusion of available water-sequestering electrolytic agents for an optimal microenvironment to be maintained during storage, with the effect of increasing shelf life and the stability of the dosage form of the delivery system. Further advantages of the delivery system disclosed include the use of only dry blend and direct compression steps, ease of transport to manufacturing sites, and reliance on only conventional tableting or encapsulation equipment for production instead of expensive specialized equipment. Because this delivery system is relatively independent of the BCs employed in formulation, targeted delivery of genetically modified bacteria or other beneficial microorganisms is also possible.

Another advantage of the present delivery system is the controlled release of the BCs such as probiotics and other bacteria from the dosage form into the surrounding environment of the GI tract. Another advantage of the present delivery system is the maintenance of a constant internal pH within the dosage form itself through the use of physiologically acceptable eletrolytic agents.

Yet another advantage of the present delivery system is the controlled exposure of the BCs such as the probiotic and other bacteria within the dosage form to aqueous media by controlling the hydration rate of the dosage form via polymer disentanglement.

Yet another advantage of the present delivery system is an increase in the stability of the delivery system in its dosage form and the viability of the biological contents by adding available water-sequestering electrolytic agents.

Yet another advantage of the present delivery system is its easy manufacturability. Either a dry-blend including a BC is directly compressed to form a tablet, or a capsule can be filled with a dry-blend including the BC. A significant advantage of the present delivery system is the absence of any processes that introduce moisture (such as enteric coating, other coating processes or granulation) or solvents, which may decrease the in vivo viability of the BCs.

In any of the embodiments mentioned previously, the delivery system can include BCs such as beneficial microorganisms, lyophilized bacteria and their associated lyophilized carrier proteins, vitamin B complex, vitamin C, other vitamins, nicotinic acid, glucosamine, chondroitin sulfate, caffeine, green tea, green tea extracts, soy isoflavones, cranberry, echinacea, other herbals, St. johns wort, alpha lipoic acid, L. carnitine, pancreatic enzymes, hormones, other enzymes or any other biologics.

The invention will best be understood by reference to the following detailed description of the preferred embodiment. The discussion below is descriptive, illustrative and exemplary and is not to be taken as limiting the scope defined by any appended claims.

BRIEF DESCRIPTION OF DRAWINGS

FIG. 13 shows the effects of physiologically acceptable eletrolytic agents on the stability of the dosage form.

DETAILED DESCRIPTION

Figure 1:
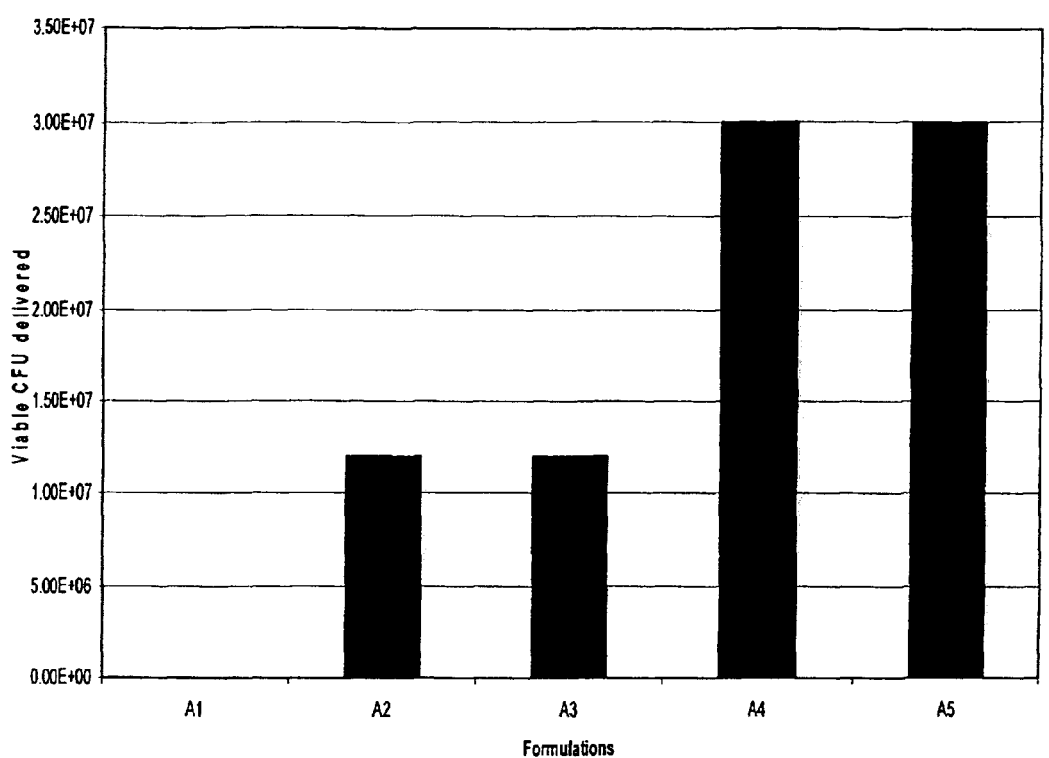
FIG. 1 shows the effects of hydrophilic agents on the controlled release of viable beneficial microorganisms into the small intestine from the delivery system in its dosage form as monolithic tablets.

A delivery system is disclosed for the controlled release of a biological component into the surrounding environment of the GI tract of humans and animals. Controlled release delivery systems include those systems capable of site specific delivery, extended release, sustained release, delayed release, repeat action, prolonged release, bimodal release, pulsitile release, modified delivery, pH sensitive delivery, and/or target specific delivery, among others. The solid dosage form may take the form of a tablet, capsule, wafer, or sachet, and is not limited to, an orally administered dosage form such as a tablet or capsule. The delivery system is minimally comprised of a delivery vehicle and a delivered component which includes the biological components.

As used herein, the delivered component, referring to biological components ("BC") include agents such as microbes, DNA, RNA, proteins, beneficial microorganisms (also known as probiotics), modified soil organisms (organisms that compete with lactic acid bacteria) bacteria, lyophilized bacteria and their associated lyophilized carrier proteins, vitamin B complex, vitamin C, other vitamins, nicotinic acid, glucosamine, chondroitin sulfate, caffeine, green tea, soy isoflavones, cranberry, echinacea, other herbals, St. johns wort, alpha lipoic acid, L. carnitine, pancreatic enzymes, hormones, other enzymes or other biologics. Vitamin B-complex includes vitamin B-1 (also known as Thiamine Mononitrate), vitamin B-2 (also known as Riboflavin), vitamin B-3 (also known as niacin), vitamin B-5 (also known as d-Calcium pantothenate), vitamin B-6 (also known as pyridoxine HCL), folic acid, biotin, vitamin B-12 (also known as cyanobalamin), choline (also known as bitartrate), and PABA (also known as Para Amino Benzoic Acid). The term "probiotic" refers to ingested microorganisms that can live in a host and contribute positively to the host's health and well being. The BC may be viable or non-viable depending on its biological activity.

As used herein, a delivery vehicle refers to a hydrophobic agent or a hydrophilic agent. For example, the delivery vehicle can have a homogenously distributed matrix, which is made up of hydrophilic agents and/or hydrophobic agents. Hydrophilic agents work by swelling, increasing viscosity, and acting as gel strength enhancers. Hydrophobic agents include waxes and other inert materials. Examples of waxes include carnauba wax, paraffin or bees wax. An example of an inert material includes ethylcellulose. More particularly, the hydrophilic agent is selected from at least one of the group, but not limited to: a) a starch selected from the group consisting of corn, rice and potato starch; b) a hydrophilic gum selected from the group consisting of tragacanth gum, locust beam gum, acacia gum, guar gum, xanthan gum, ghatti gum and galactomannan gum; c) a cellulose derivative selected from the group consisting of methylcellulose, carboxymethylcellulose, sodium starch glycollate, sodium or calcium carboxymethylcellulose, hydroxyethyl methylcellulose, hydroxypropyl methylcellulose, ethylhydroxy ethylcellulose, ethylmethylcellulose, hydroxyethylcellulose and cellulose acetate phthalate; d) a desiccant selected from the group consisting of silica, aluminum silicate, magnesium silicate, aluminum magnesium silicate, sodium silicate and feldspar; e) aluminum hydroxide; f) a polypeptide selected from the group consisting of gelatin, collage, casein and heterogeneous protein mixture; g) an algae derivative selected from the group consisting of alginic acid, sodium alginate, agar, dextran and carageenan; h) a polymer selected from the group consisting of acrylate, carboxypolymethylene, a polyalkylene glycol and polyvinylpyrrolidone; and i) a polysaccharide selected from the group consisting of pectin and maltodextrin. In another aspect, the hydrophilic agents are also selected from the group of cellulose derivatives such as microcrystalline cellulose (MCC), hydroxypropyl methylcellulose (HPMC) and hydroxypropyl cellulose (HPC), or from gums and polysaccharides such as guar gum or maltodextrin. These hydrophilic agents such as MCC, HPMC, HPC or maltodextrin are associated with lower levels of control to achieve a certain matrix viscosity.

As used herein, the delivery system may optionally include a release-modifying agent added to aid in bypassing the stomach ("gastric bypass") or to modify the release profile of the BC due to pH-specific swelling characteristics or site-specific enzyme degradation within the GI tract. These release modifying agents or release modifying excipients may include but are not limited to at least one of alginate, polysaccharides such as such as gelatin or collagen, guar gum, xanthan gum, pectin, heterogeneous protein mixtures, and polypeptides. The polysaccharides may be pectin and/or an alginate salt, among others. The galactomannan gums may be guar gum, xanthan gum and/or locust bean gum, among others. The polyethylene derivatives may be polyethylene oxide (PEO) and/or polyethylene glycol (PEG), among others. The hydrolyzed proteins may be gelatin and/or collagen, among others. The polypeptides or proteins may be gelatin, collagen, casein, or a heterogenous protein mixture.

As used herein, the electrolytes or electrolytic agents may be at least one of sodium, potassium, or calcium salts, among others. Through the inclusion of physiologically acceptable electrolytic agents, the buffered environment allows reconstitution and release to occur under optimal pH conditions for BC viability. The interaction between an electrolytic agent and a hydrophilic agent may allow not only the pH-independent release of the BC, but also allows for the internal pH of the dosage form to remain constant. It is this constant internal pH that contributes significantly to the stability of the BC in-vivo.

Optionally, physiologically acceptable salts or electrolytic agents may be introduced to the bacterial freeze-dried product (FDP) during lyophilization at a ratio of 1.0:0.1 to 1.0:25 bacterial FDP to salt. The delivery system ensures the maintenance of a constant pH within the dosage form itself and acts as a cryoprotectant during the freeze-drying process to prevent lysing of the BCs.

As used herein, the delivery system may optionally include a desiccant. The desiccant may include, but is not limited to, sodium carboxymethylcellulose, calcium carboxymethylcellulose, colloidal silica dioxide, and combinations thereof. The disintegration agent may include, but is not limited to, croscarmellose sodium sold as Solutab™ available from Blanver Farmoquimica LTDA and crosprovidone (insoluble polyvinylpyrrolidone) sold as Kollidon CL™ available from BASF.

As used herein, the delivery system may optionally include flow and tubing agents. The flow agents may include, but are not limited to, magnesium stearate and stearic acid. Flow or tubing agents may be used to improve the manufacturability. This addition of flow or tubing agents may also result in decreased loss of viability of BCs during the manufacturing process due to compression and heat resulting from powder flow, tableting, and encapsulation.

In a first embodiment, the delivery system includes a swelling hydrophilic agent and a BC. It is based on the homologous distribution of the various components within a solid matrix dosage form. The delivery system allows for a controlled exposure of the BC within the dosage form to an aqueous media by controlling the hydration rate of the dosage form via polymer disentanglement and matrix erosion. Optionally, the delivery system may also include a physiologically acceptable electrolytic agent, a release modifying agent, a desiccant, and flow or tubing agents, alone or in combination. Electrolytic agents can provide a mechanism for available water-sequestration to increased stability of the dosage form and the viability of its contents, particularly the BC. Desiccants may also be used to sequester available water for a similar purpose. The release modifying agents, such as gums and polysaccharides, may be used to induce site-specific release through pH-specific swelling or site-specific enzymatic degradation.

In one aspect of the embodiment, the BC may be a probiotic pre-blend of powders, which can be blended with a carrier. The carrier may be, but is not limited to, monosaccharides or polysaccharides, swellable polymers, inert fillers or other inert substances. The monosaccharides or polysaccharides, including but not limited to, maltodextrin can be used. The swellable polymers, including but not limited to, hydroxypropyl methylcellulose, can be used. The inert fillers, including but not limited to, microcrystalline cellulose or di-calcium phosphate can be used. Other inert materials, including carnauba wax, can be used. In the aspect wherein a carrier is included, the carrier may function to assist in the controlled release of the BCs, to aid in the manufacturability of the dosage form, or to increase the stability of the dosage form.

The delivery system can be a readily manufacturable solid dosage form. In one aspect, the dosage form is in the form of a monolithic tablet or a capsule. When a tablet or a capsule, it may be administered orally, anally, and vaginally, among other routes. In one aspect, the dosage form is a monolithic tablet created from a direct-compressible dry blend which does not require processes, such as enteric coating, granulation, or spray drying, that expose the BC to temperatures that might cause any biological components to be damaged. However, provided such coating or granulation processes are carried out in a manner that do not damage the BCs, nor adversely affect the hydration state of the matrix, they may be amenable.

Release of the BC into the surrounding environment may be accomplished through a rate-controlled hydration and subsequent swelling of hydrophilic agents. The release of the BC is determined by the erosion rate and polymeric disentanglement of the swollen hydrophilic matrix. Without subscribing to a particular theory of kinetics, the swelling of the hydrophilic matrix is retarded by a plurality of layers of viscous gelled hydrophilic agents. These gel-states result from the interaction of the hydrophilic agents with the penetrating GI fluid. While primarily erosion dependent, the gradual hydration and gelling reaction within the hydrophilic matrix allows for a highly reproducible, programmable release pattern. The programmability of the delivery system allows for nearly any physiologically relevant release pattern to be accomplished.

Mathematical treatment of the hydrophilic matrix swelling, erosion, and ensuing release of BC can be determined, though each model will be representative of the particular components specific to each formulation. This can be accomplished without the need for undue experimentation.

Formulation specific to the physical characteristics of each BC and the desired release profile can be accomplished through both theoretical and empirical means, allowing dissolution of the delivery system and BC release to occur in a specific physiologic region. Release of BCs from the delivery system in a given region of the GI tract is accomplished by the slowly hydrating hydrophilic matrix containing the biological activities segregated from the external environment until the desired physiologic region of release may be employed such as to achieve gastric bypass. Consideration of both the area and duration of release is essential in formulation so as to program the delivery system with an appropriate ratio of components to ensure the desired release profile.

The homologous distribution of BCs within the hydrophilic matrix provides protection from the fluctuations in pH and exposure to enzymatic degradation present in external environment of the GI tract. When the BCs such as lyophilized microorganisms are delivered, this isolation from the outside environment allows the microorganisms to remain in lyophilized stasis significantly longer than with conventional immediate release dosage forms.

In another embodiment, when physiologically acceptable electrolytic agents are included into the delivery system, the electrolytic agent maintains an intra-dosage form pH, irrespective of the external pH of the GI environment. This internal pH of the delivery system in its dosage form may be modified through the selection of electrolytic agents that are both physiologically-acceptable for human consumption and physiologically-appropriate to individual BCs. When delivering lyophilized BCs, this internal pH may be selected to create an optimal environment for the reconstitution of the lyophilized BCs. Such an environment may result in an increase in viability during the reconstitution process, and moreover, may limit the exposure of the lyophilized BCs to fluctuations in the pH ranges of the GI tract, resulting in an increase in microorganism viability while the matrix is in a hydrated state and prior to the BCs release into the environment.

The addition of physiologically-acceptable electrolytic agents may also be employed to aid in available water-sequestration. When delivering BCs such as lyophilized beneficial microorganisms, this addition of the electrolytic agent is especially useful because interactions with any available water, such as the available water present in the constituent controlling excipients, flow agents and desiccants, may result in inadvertent, premature reconstitution prior to release of the BCs into the GI environment. Premature reconstitution from a lyophilized state causes the microorganisms to begin metabolizing available sources of energy. The constituents of the delivery system provide very limited sources of energy. When these locally available sources of energy are exhausted, the microorganisms expire. The metabolic byproducts of prematurely reanimated microorganisms may also have a negative impact on the viability of the remaining, non-reanimated microorganisms. When disposed in a homogeneous manner throughout the dosage form, the electrolytic agents that have a higher degree of hydrophilicity than the other constituents of the delivery system surrounding them, may preferentially hydrate, decreasing or preventing the re-hydration of the lyophilized agents. An example of a delivery system not including an electrolytic agent is a delivery system that is dependent upon erosion as its release mechanism, or one in which the maintenance of a constant pH range within the dosage form is not desired. The BCs such as lyophilized microorganisms and hydrophilic agents do not require an electrolytic agent to make a controlled release dosage form capsule. Another example that does not require an electrolytic agent is where the controlled release of non-viable BCs (such as non-viable bacterial biomass) is sought as the primary function of the dosage form.

In another embodiment of the delivery system, the addition of a release modifying agent, such as hydrophilic polymers or gums demonstrating pH or enzyme sensitivity, may be employed to alter the swelling or erosion characteristics of the matrix, such as the initiation of swelling or the rate of erosion of the matrix. These release modifying agents function in combination with the hydrophilic agent to control the release of the BC. These release modifying agents may be employed to reduce the amount of exposure to the gastric environment by reducing matrix swelling during exposure to the pH ranges of the stomach or during the time the dosage form is expected to transit through the stomach and pylorus. These release modifying agents may be selected for their in vivo degradation characteristics that occur in localized regions of the GI tract.

The release modifying agent, when used alone, may function as the hydrophilic agent. One example of this, among many, is that pectin mainly breaks down at the higher pH and enzyme rich environment of the large intestine. Thus, it can be employed alone as the hydrophilic agent if a greater proportion of lower intestinal tract delivery was desired, such as targeting the large intestine. Another example among others is that gelatin largely breaks down in the small intestine. With regards to pharmaceutical controlled release formulations, the location of polymer breakdown is of special significance because bioavailability is determined by the amount of drug released within a given timeframe relative to a physiological site of absorption specific to that type of compound. The delivery of BCs is essentially similar in intent, given localized sites for absorption and adsorption. When delivering BCs, the inclusion of release modifying agents whose swelling characteristics are pH dependent, specifically compounds that preferentially swell in environments above pH 1.0-1.5, is useful for the delivery of BCs such as lactic acid bacteria, a probiotic. Lactic acid bacteria are particularly susceptible to viability losses when exposed to low pH. The low-pH environment will inhibit swelling, thus retarding both BC release and acid-penetration into the dosage form. The inclusion of release modifying agents whose erosion is enzyme-dependent, specifically compounds that degrade preferentially in the presence of lower intestinal tract enzymes, is useful for the delivery of lactic acid bacteria in which the attachment site for the lactic acid bacteria is distal to the location of the enzymes.

In yet another embodiment of the invention, the delivery system is a pore-forming wax matrix composed of one or more inert insoluble waxes considered to be hydrophobic agents, polymers or inert fillers in which is disposed pore forming excipients and the BC, such as active lyophilized bacteria and their associated lyophilized carrier proteins. Hydrophilic agents may be included with hydrophobic agents to make pore forming wax matrices.

In yet another embodiment, the delivery system may include a multi-particulate plurality of granules, coated beads or coated non-pareils which are distributed within the dosage form in either an active polymer matrix or immediate release matrix for the purposes of controlled release of the lyophilized active ingredients.

In one embodiment, the dosage form disclosed is formed from a pre-blend of powders. When making the delivery system in its form of a monolithic tablet, the pre-blend of powders is mixed with the BCs using dry-blend techniques known to those skilled in the art, and the dosage form is created using a direct compression process. Employing a pre-blend that is formed using dry-blend techniques is a significant improvement over the use of blends resulting from granulation, spheronization-extrusion, or other coating processes that might expose the BCs to moisture or solvents and potentially lower the viability of the BCs. Employing a pre-blend that is capable of forming a dosage form using only the techniques of direct-compression or high-speed encapsulation, in the case of a monolithic tablet or a capsule, is a significant improvement over manufacturing processes that require multi-stage compression, multiple geometrically-altered components or coatings, including enteric coating, that might expose the BC to hazardous environmental conditions such as solvents, high forces of compression, excessive heat or undue physical stress. When delivering BCs such as lyophilized microorganisms, it is important to maintain the in vivo viability of the lyophilized microorganisms and preventing the premature reconstitution of the microorganims in the delivery system.

The dosage form disclosed may be formed from a pre-blend of powders. For example, BCs such as lyophilized beneficial microorganisms, are mixed with a pre-blend of one or more controlling agents, inert fillers, desiccants, and flow agents that have been mechanically, chemically, or otherwise dried to reduce the available water present for the purpose of preventing undesirable interactions of the BCs and hydrophilic agents with any available water within the dosage form. The minimization of available water within the dosage form is intended to prevent unintentional or pre-mature reconstitution of the lyophilized BCs. The use of a pre-blend in which the non-lyophilized BCs are dried and subsequently blended with the lyophilized BCs, while not necessary for the creation of a controlled release dosage form, is a significant improvement over the use of non-dried components or the drying of a pre-blend of powders containing both lyophilized and non-lyophilized BCs. The non-dried components may contain enough available water to induce pre-mature reconstitution prior to in vivo release. The drying of the pre-blend exposes the lyophilized BCs to undue heat and may extensively reduce their in vivo viability.

Unless otherwise noted, all of the following embodiments are formulated through standard dry blend and directly compressed with an appropriate lubricant or flowing agent such as magnesium stearate or stearic acid.

In the first embodiment, a formulation is disclosed for a delivery system by combining the BC such as lyophilized bacteria (freeze-dried) powder pre-blend (FDP) with a suitable hydrophilic agent such as HPMC, MCC, or PEO, in a ratio of about 1.0:0.1 to 1:25 FDP to hydrophilic agent.

In the second embodiment, a formulation is disclosed for making a delivery system by including bacterial FDP, hydrophilic agent, and a physiologically acceptable electrolytic agent such as $NaHCO_3$, $Na2CO_3$, or $CaCO_3$, in a ratio of about 1.0:0.1:0.1 to 1:25:25 FDP to hydrophilic agent to electrolytic agent.

The third embodiment, a formulation is disclosed for making a delivery system by including bacterial FDP, a hydrophilic agent, and a release modifying agent in the form of a hydrophilic polysaccharide such as pectin, sodium alginate alginic acid, or a gum such as xanthan gum, guar gum, locust bean gum, or tragacanth gum, in a ratio of about 1.0:0.1:0.1 to 1:25:25 FDP to hydrophilic agent to polysaccharide or gum.

The fourth embodiment, a formulation is disclosed for a delivery system by including bacterial FDP, a hydrophilic agent, a release modifying agent in the form of a hydrophilic polysaccharide or gum, and a physiologically acceptable salt in a ratio of about 1.0:0.1:0.1:0.1 to 1:25:25:25 FDP to hydrophilic agent to polysaccharide or gum to electrolytic agent.

The fifth embodiment, a formulation is disclosed for a delivery system by including bacterial FDP, a hydrophilic agent, a release modifying agent, in the form of a hydrophilic polysaccharide or gum, a physiologically acceptable salt, and an inert filler in a ratio of about 1.0:0.1:0.1:0.1:0.1 to 1:25:25:25 FDP to hydrophilic agent to polysaccharide or gum to electrolytic agent to inert filler.

In the sixth embodiment, a formulation is disclosed for a delivery system by combining the BC such as lyophilized lactic acid bacteria pre-blend with a suitable hydrophobic agent such as carnauba wax, in a ratio of about 1.0:0.1 to 1:25 FDP to hydrophobic agent.

In the seventh embodiment, a formulation is disclosed for a delivery system by including a bacterial FDP, a hydrophobic agent, and a physiologically acceptable salt such as $NaHCO_3$, $Na2CO_3$, or $CaCO_3$, in a ratio of about 1.0:0.1:0.1 to 1:25:25 FDP to hydrophobic agent to electrolytic agent.

In the eighth embodiment, a formulation is disclosed for a delivery system by including bacterial FDP, a hydrophobic agent, a physiologically acceptable electrolytic agent such as $NaHCO_3$, $Na2CO_3$, or $CaCO_3$, and a release modifying agent, in the form of a hydrophilic polysaccharide such as pectin, sodium alginate alginic acid, or a gum such as xanthan gum, guar gum, locust bean gum, or tragacanth gum, in a ratio of about 1.0:0.1:0.1:0.1 to 1:25:25:25 FDP to hydrophobic agent to polysaccharide or gum to electrolytic agent.

In the ninth embodiment, a formulation is disclosed for a delivery system by including Green Tea Extract as a biological component; a hydrophilic agent in the form of HPMC, MCC or PEO; a release modifying agent in the form of a hydrophilic polysaccharide such as pectin, sodium alginate, alginic acid or a gum such as xanthan gum, guar gum, locust bean gum, or tragacath gum; and a physiologically acceptable electrolytic agent such as $NaHCO_3$, $Na_2CO_3$, or $CaCO_3$, in a ratio of about 1.0:1.0:0.75:0.25 to 1:25:25:25 biological component to hydrophyilic agent to release modifying agent to electrolytic agent.

In the tenth embodiment, a formulation is disclosed for a delivery system by including Alpha Lipoic Acid (ALA) and L. carnitine as biological components; a hydrophilic agent in the form of HPMC, MCC or PEO; a release modifying agent in the form of a hydrophilic polysaccharide such as pectin, sodium alginate, alginic acid or a gum such as xanthan gum, guar gum, locust bean gum, or tragacath gum; and a physiologically acceptable electrolytic agent such as $NaHCO_3$, $Na_2CO_3$, or $CaCO_3$, in a ratio of about 1.0:0.7:0.15:0.2 to 1:25:25:25 biological component to hydrophyilic agent to release modifying agent to electrolytic agent.

In the eleventh embodiment, a formulation is disclosed for a delivery system by including Soy isoflavanes as biological components; a hydrophilic agent in the form of HPMC, MCC or PEO; a release modifying agent in the form of a hydrophilic polysaccharide such as pectin, sodium alginate, alginic acid or a gum such as xanthan gum, guar gum, locust bean gum, or tragacath gum; and a physiologically acceptable electrolytic agent such as $NaHCO_3$, $Na_2CO_3$, or $CaCO_3$, in a ratio of about 1.0:1.0:0.75:0.25 to 1:25:25:25 biological component to hydrophyilic agent to release modifying agent to electrolytic agent.

In the twelfth embodiment, a formulation is disclosed for a delivery system by including caffeine as a biological component; a hydrophilic agent in the form of HPMC, MCC or PEO; a release modifying agent in the form of a hydrophilic polysaccharide such as pectin, sodium alginate, alginic acid or a gum such as xanthan gum, guar gum, locust bean gum, or tragacath gum; and a physiologically acceptable electrolytic agent such as $NaHCO_3$, $Na_2CO_3$, or $CaCO_3$, in a ratio of about 1.0:2.0:0.75:0.50 to 1:25:25:25 biological component to hydrophyilic agent to release modifying agent to electrolytic agent.

In the thirteenth embodiment, a formulation is disclosed for a delivery system by including B-complex as a biological component; a hydrophilic agent in the form of HPMC, MCC or PEO; a release modifying agent in the form of a hydrophilic polysaccharide such as pectin, sodium alginate, alginic acid or a gum such as xanthan gum, guar gum, locust bean gum, or tragacath gum; and a physiologically acceptable electrolytic agent such as $NaHCO_3$, $Na_2CO_3$, or $CaCO_3$, in a ratio of about 2.0:1.0:0.1:0.1 to 1:25:25:25 biological component to hydrophyilic agent to release modifying agent to electrolytic agent.

The dosage forms may be monolithic tablets, capsules, wafers, sachets, gelatin or vegetable capsules for oral, anal, or vaginal delivery systems.

Methods

The formulations of the delivery system described below have been prepared in accordance with the following methods. In these formulations, the dosage form in tablets were prepared using a method of dry blending and direct compression using a Carver hydraulic press or a rotary tablet press. Evaluations were performed using a USP Type II (paddle) dissolution apparatus.

Examples 1-5, 9, 10, and 12 were conducted by exposing the dosage forms to 1000 mL 0.1 NHCl for 2 hours at 50 RPM. The dosage forms were then removed and placed into peptone buffer medium and stomached, (the dosage form is crushed and homogenized within the buffer media for the purpose of enumerating the remaining bacteria in the tablet), after which a sample was taken from the dissolution media. The samples were then plated on MRS and RCM media to discern viable colony forming units (CFU).

Example 6 was performed by exposing the dosage forms to 1000 mL USP HCl for 2 hours at 50 RPM. The dosage forms were removed and placed into $KH_2PO_4$ buffer dissolution medium and the dissolution media was sampled at regular intervals. The samples were then plated on MRS and RCM media to discern viable colony forming units (CFU).

Examples 7 and 8 were performed by exposing the dosage forms to 1000 mL USP HCl (Ex. 7) or 0.1N HCl (Ex. 8) for 2 hours at 50 RPM. The dosage forms were removed and placed into $KH_2PO_4$ (Ex. 7) or peptone (Ex. 8) buffer medium and the dissolution media was sampled at regular intervals. The samples were then filtered, reacted with 4',6-diamidino-2-phenylindole, and enumerated under UV-light.

Example 11 was performed using the dosage forms as tablets produced from excipients desiccated in a fluid bed drier, mixed with the BCs such as the lactic acid bacteria pre-blend and flow agents. The dosage forms were then exposed to 1000 mL 0.1N HCl for 2 hours at 50 RPM. The dosage forms were removed and placed into peptone buffer medium and stomached, after which the dissolution media was sampled. The samples were then plated on MRS and RCM media to discern viable colony forming units (CFU).

Example 13 was performed using dosage forms packaged in foil sachets and exposed to ambient environmental conditions (25 degrees C., 60% Relative Humidity) for 4 months and subsequently tested. The samples were removed to peptone buffer solution, stomached, and plated on MRS and RCM media to discern viable colony forming units (CFU).

Example 1

A delivery system in its dosage form as a monolithic tablet, approximately 382 mg, containing a hydrophilic agent and biological component (BC) was prepared as shown in Table 1. The group A1 is the control. In this example, the BC is comprised of beneficial microorganism such as the lactic acid bacteria pre-blend of lyophilized powder and starch. The hydrophilic agent employed is microcrystalline cellulose (MCC), maltodextrin, hydroxypropyl methylcellulose (HPMC), or polyethylene oxide (PEO). The addition of the hydrophilic agent will retard the release of the BC from the dosage form. Stearic acid is included as a flow agent and silica is employed as flow agent and desiccant.

As shown in FIG. 1, the results of this example reflect a level of controlled release granted through the use of a matrix comprised of a hydrophilic agent and the lyophilized BC. This controlled release is shown through a much higher level of viable lactic acid bacteria colony forming units (CFU) delivered after exposure to gastric media than the control. The use of less swellable hydrophilic agents such as MCC and maltodextrin are associated with sufficient, but lower levels of control. A superior level of control is demonstrated in both polyethylene oxide and HPMC matrices. Thus, the hydrophilic agent is not limited to a particular type of hydrophilic agent, so long as sufficient matrix viscosity is achieved.

TABLE 1

|  | Dosage Formulas (mg) | | | | |
| --- | --- | --- | --- | --- | --- |
|  | A1 (CTRL) | A2 | A3 | A4 | A5 |
| Lactic acid bacteria pre-blend | 150 | 150 | 150 | 150 | 150 |
| HPMC | 0 | 0 | 0 | 200 | 0 |
| PEO | 0 | 0 | 0 | 0 | 200 |
| MCC | 0 | 200 | 0 | 0 | 0 |
| Maltodextrin | 0 | 0 | 200 | 0 | 0 |
| Stearic Acid | 16 | 16 | 16 | 16 | 16 |
| Silica | 16 | 16 | 16 | 16 | 16 |
| TOTAL WEIGHT | 182 | 382 | 382 | 382 | 382 |

Example 2

A delivery system in its dosage form as a monolithic tablet of approximately 382 mg, containing a hydrophilic agent, an electrolytic agent, and a BC, was prepared as set forth in Table 2. The group B1 is the control. The formulation employs HPMC as the hydrophilic agent. The electrolytic agents used includes any one of the NaHCO$_3$, Na$_2$CO$_3$ or NaH$_2$PO$_4$. The BC, in this case, consists of lactic acid bacteria pre-blend of lyophilized powder and starch. The addition of the electrolytic agent, any one of NaHCO$_3$, Na$_2$CO$_3$ or NaH$_2$PO$_4$, establishes the internal pH within the dosage form of the delivery system. Stearic acid is included as a flow agent and silica is employed as flow agent and desiccant.

Figure 2:
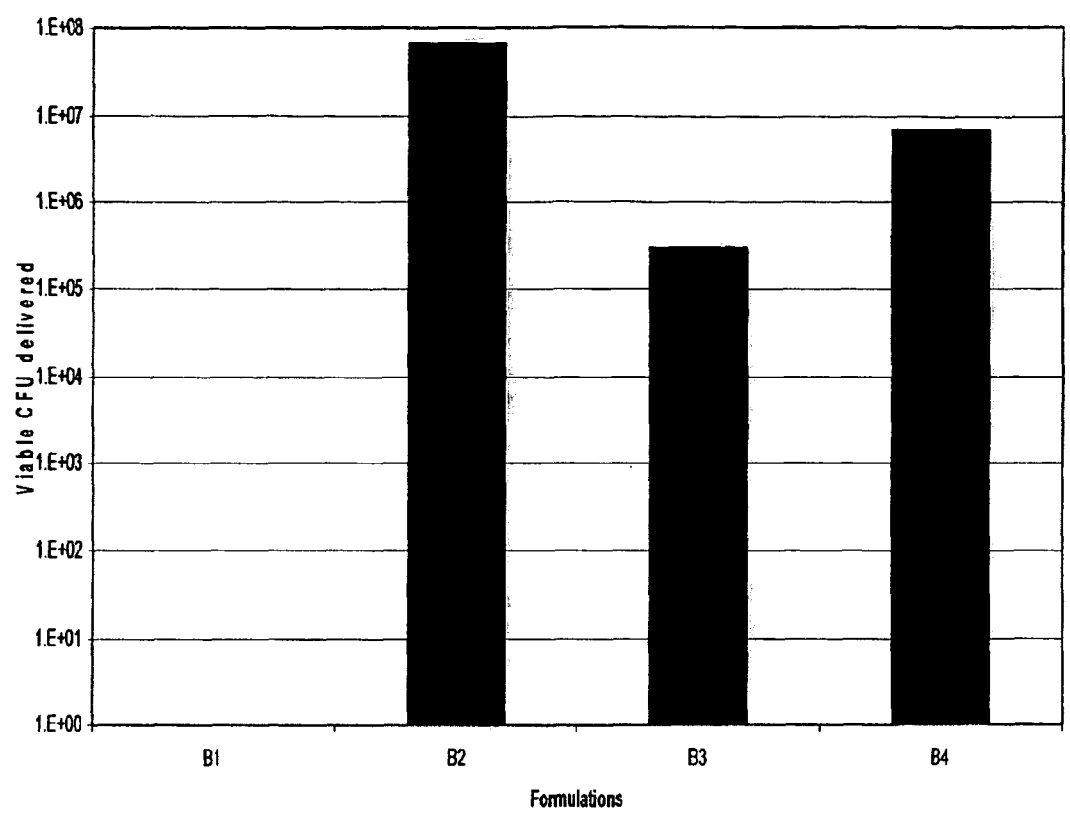
FIG. 2 shows the effects of the addition of electrolytic agents on the controlled release of viable beneficial microorganisms into the small intestine from the delivery system in its dosage form as monolithic tablets.

This example demonstrates, as shown in FIG. 2, that the internal pH of the dosage form is altered by the presence of the electrolytic agent, affecting the amount of viable CFU delivered. This establishment of a particular internal pH is associated with differing levels of viability for a given reconstituted lyophilized BC. In particular, formulation B2 contains Na$_2$CO$_3$ and the electrolytic agent provides an internal pH within the dosage form of the delivery system and aids in the reconstitution of viable lactic acid bacteria.

TABLE 2

|  | Dosage Formulas (mg) | | | |
| --- | --- | --- | --- | --- |
|  | B1 (ctrl) | B2 | B3 | B4 |
| Lactic acid bacteria pre-blend | 150 | 150 | 150 | 150 |
| HPMC | 00 | 100 | 100 | 100 |
| NaHCO$_3$ | 0 | 100 | 0 | 0 |
| NaHCO$_3$ | 0 | 0 | 100 | 0 |
| NaH$_2$PO$_4$ | 0 | 0 | 0 | 100 |
| Stearic Acid | 16 | 16 | 16 | 16 |
| Silica | 16 | 16 | 16 | 16 |
| TOTAL WEIGHT | 182 | 382 | 382 | 382 |

Example 3

A delivery system in its dosage form as a monolithic tablet of approximately 382 mg containing a hydrophilic agent, a release-modifying agent, and a BC was prepared as shown in Table 3. The group C1 is the control. The hydrophilic agent employed is HPMC. The release-modifying agent employed is pectin or gelatin. The lactic acid bacteria pre-blend of lyophilized powder and starch makes up the BC. Stearic acid is included as a flow agent and silica is employed as flow agent and desiccant.

Figure 3:
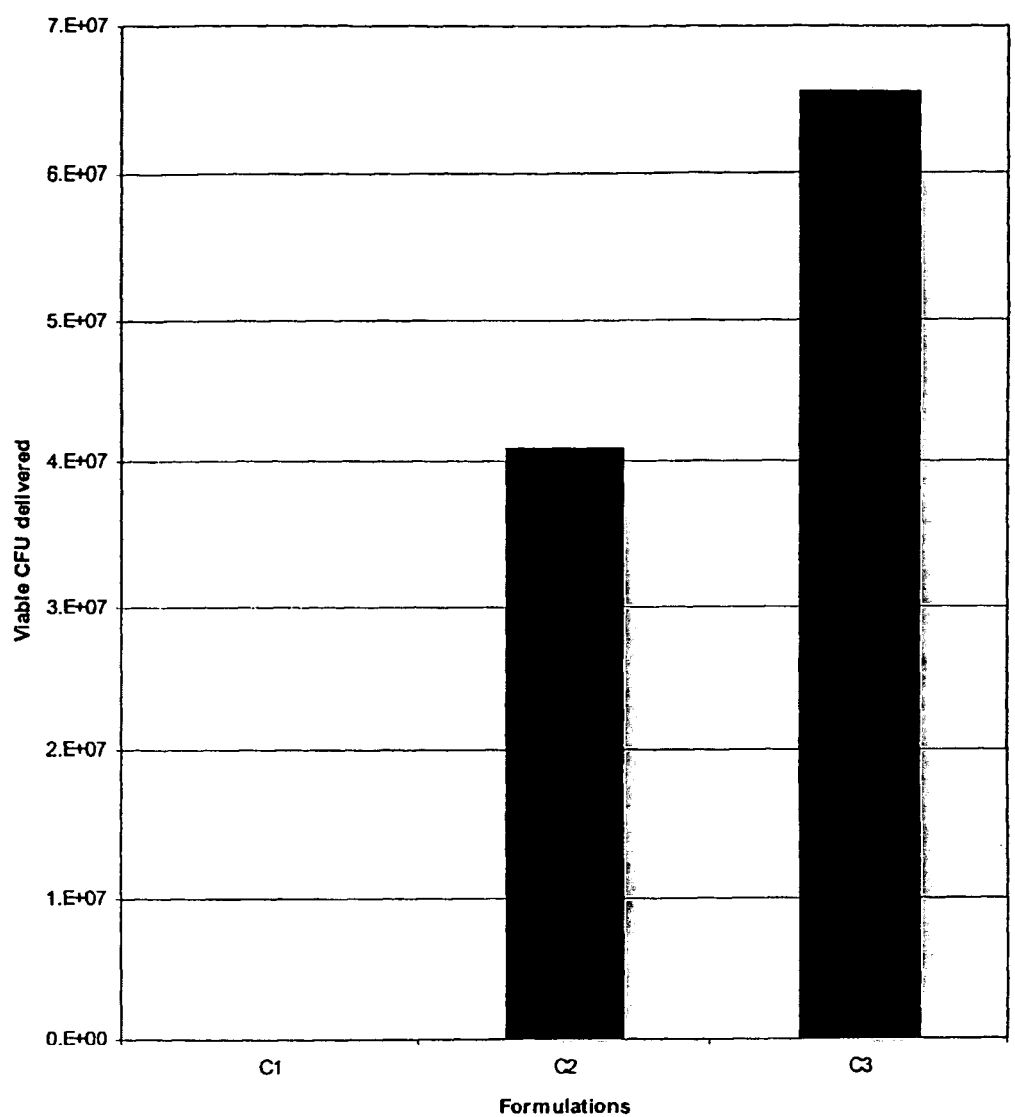
FIG. 3 shows the effects of the addition of pH and enzyme-sensitive agents on the controlled release of viable beneficial microorganisms into the small intestine from the delivery system in its dosage form as monolithic tablets.

This example illustrates, as shown in FIG. 3, an increased level of control that is possible when the release modifying agent is added to a hydrophilic swellable matrix. The presence of pectin or gelatin as the release modifying agent is associated with a degree of pH-dependent degradation and an overall increase in matrix viscosity which retards the release of the BC. This is reflected in the increase in viable CFU delivered after exposure to the gastric pH media.

TABLE 3

|  | Dosage Formulas (mg) | | |
| --- | --- | --- | --- |
|  | C1 (CTRL) | C2 | C3 |
| Lactic acid bacteria pre-blend | 150 | 150 | 150 |
| HPMC | 0 | 100 | 100 |
| Pectin | 0 | 100 | 0 |
| Gelatin | 0 | 0 | 100 |
| Stearic Acid | 16 | 16 | 16 |
| Silica | 16 | 16 | 16 |
| TOTAL WEIGHT | 182 | 382 | 382 |

Example 4

A delivery system in its dosage form as a monolithic tablet of approximately 382 mg containing a hydrophilic agent and a BC was prepared as shown in Table 4. The group C1 is the control. The hydrophilic agent employed is pectin. The lactic acid bacteria pre-blend of lyophilized powder and starch make up the BC. Stearic acid is included as a flow agent, and silica is employed as a flow agent and desiccant.

Figure 4:
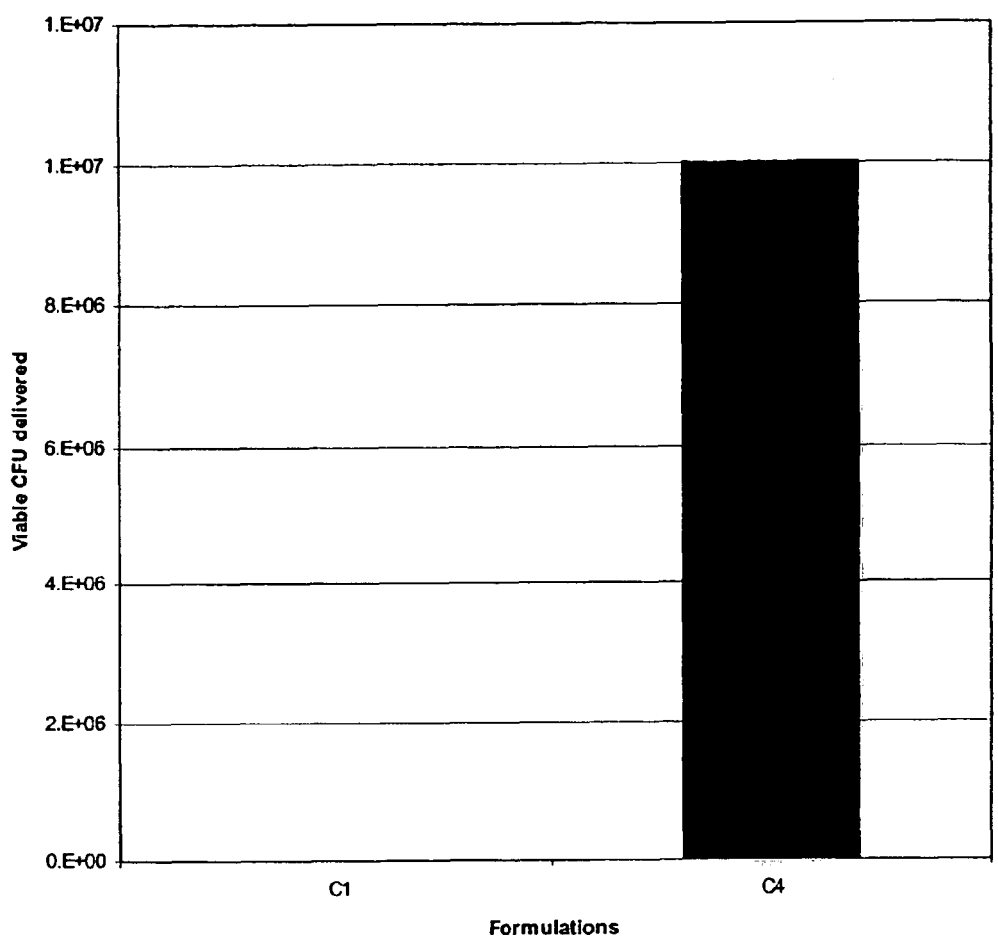
FIG. 4 shows the effects of the addition of pH- and enzyme-sensitive agents on the controlled release of viable beneficial microorganisms into the small intestine from the delivery system in its dosage form as monolithic tablets.

This example illustrates, as shown in FIG. 4, a level of control possible when employing a hydrophilic agent that displays pH-dependency and enzyme-dependent degradation. This example also illustrates the use of a release modifying agent as a hydrophilic agent. The presence of pectin as the release modifying agent is also associated with an overall increase in matrix viscosity which retards the release of the BC. This is reflected in the increase in viable CFU delivered after exposure to the acidic gastric pH media.

TABLE 4

| Dosage Formulas (mg) | C1 (CTRL) | C4 |
|---|---|---|
| Lactic acid bacteria pre-blend | 150 | 150 |
| Pectin | 0 | 200 |
| Stearic Acid | 16 | 16 |
| Silica | 16 | 16 |
| TOTAL WEIGHT | 182 | 382 |

Example 5

A delivery system in its dosage form as a monolithic tablet of approximately 482 mg containing a hydrophilic agent, a release-modifying agent, an electrolytic agent, and a BC was prepared as shown in Table 5. The group D1 is the control. The hydrophilic agent employed is guar gum. The release-modifying agent employed is pectin. The electrolytic agent used is $NaHCO_3$. The BC employed is comprised of the lactic acid bacteria pre-blend of lyophilized powder and starch. Stearic acid is included as a flow agent and silica is employed as a flow agent and desiccant.

Figure 5:
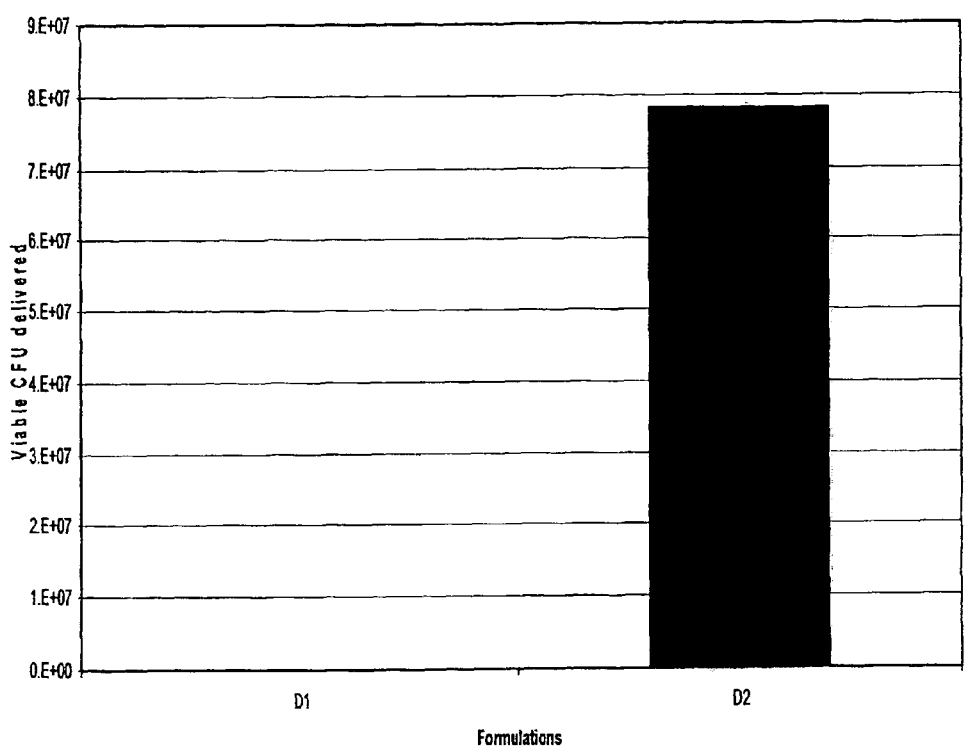
FIG. 5 shows the effects of electrolytic agents and pH and enzyme-sensitive agents on the controlled release of viable beneficial microorganisms into the small intestine from the delivery system in its dosage form as monolithic tablets.

This example illustrates, as shown in FIG. 5, the application of galactomannan gum as the hydrophilic agent in combination with a sodium salt as the electrolytic agent and a polysaccharide in a hydrophilic swellable matrix. The presence of a galactomannan gum as the hydrophilic agent is associated with an overall increase in matrix viscosity which retards the release of the BC. The presence of $NaHCO_3$ as the electrolytic agent is associated with internal pH modulation favorable to the reconstitution of lactic acid bacteria. This is reflected in the increase in viable lactic acid CFU delivered after exposure to the acidic pH ranges of the gastric media.

TABLE 5

| Dosage Formulas (mg) | D1 (CTRL) | D2 |
|---|---|---|
| Lactic acid bacteria pre-blend | 150 | 150 |
| Guar | 0 | 100 |
| $NaHCO_3$ | 0 | 100 |
| Pectin | 0 | 100 |
| Stearic Acid | 16 | 16 |
| Silica | 16 | 16 |
| TOTAL WEIGHT | 182 | 482 |

Example 6

A delivery system in its dosage form of a monolithic tablet of approximately 443 mg containing a hydrophilic agent, an electrolytic agent, a release-modifying agent, an inert filler, and a BC was prepared as shown in Table 6. The hydrophilic agent employed is HPMC. The electrolytic agent used is $NaHCO_3$. The release-modifying agent employed is pectin, and the inert filler employed is MCC. The BC employed in this example consists of the lactic acid bacteria pre-blend of lyophilized powder and starch. The addition of inert filler is associated with increased power flowability which is often advantageous during the manufacturing process. Stearic acid is included as a flow agent, and silica is employed as a flow agent and desiccant. Turmeric is included as a colorant.

Figure 6:
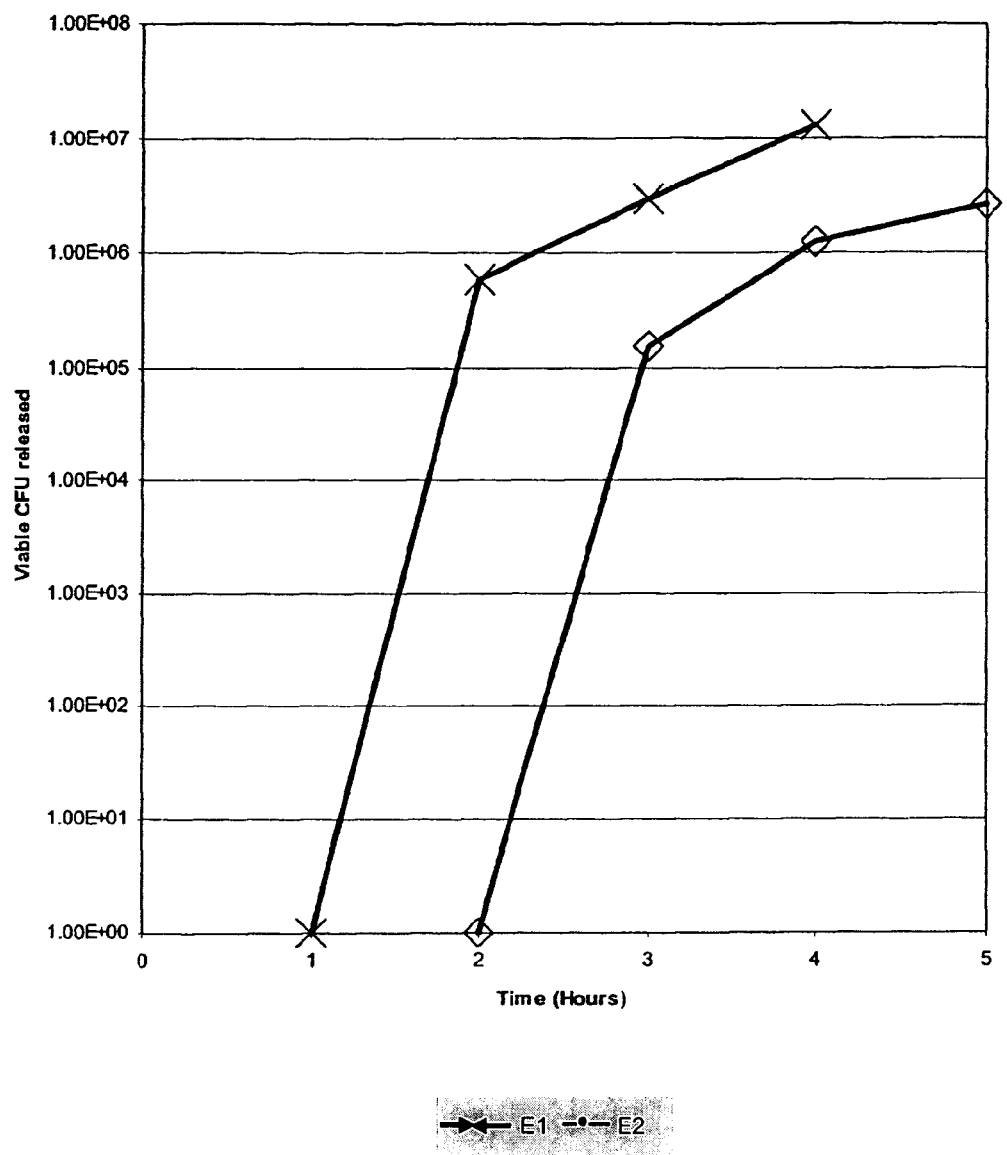
FIG. 6 shows the capacity for the controlled release of viable beneficial microorganisms over extended durations from the delivery system in its dosage form as monolithic tablets.

As depicted in FIG. 6, the results of this example demonstrate the capacity for the controlled release of viable BCs over an extended duration. The controlled release of the hydrophilic matrix is also shown to perform similarly regardless of the duration of exposure to gastric media. E1 and E2 are identical formulations showing the difference in controlled release based upon a 1 hour, or 2 hour exposure time, respectively.

TABLE 6

| Dosage Formulas (mg) | E1 | E2 |
|---|---|---|
| Lactic acid bacteria pre-blend | 150 | 150 |
| HPMC | 50 | 50 |
| $NaHCO_3$ | 50 | 50 |
| MCC | 200 | 200 |
| Pectin | 50 | 50 |
| Stearic Acid | 16 | 16 |
| Silica | 16 | 16 |
| Turmeric | 2 | 2 |
| TOTAL WEIGHT | 443 | 443 |

Example 7

A delivery system in its dosage form as a monolithic tablet of approximately 443 mg containing a hydrophilic agent, an electrolytic agent, a release-modifying agent, an inert filler, and a BC was prepared as shown in Table 6.

Figure 7:
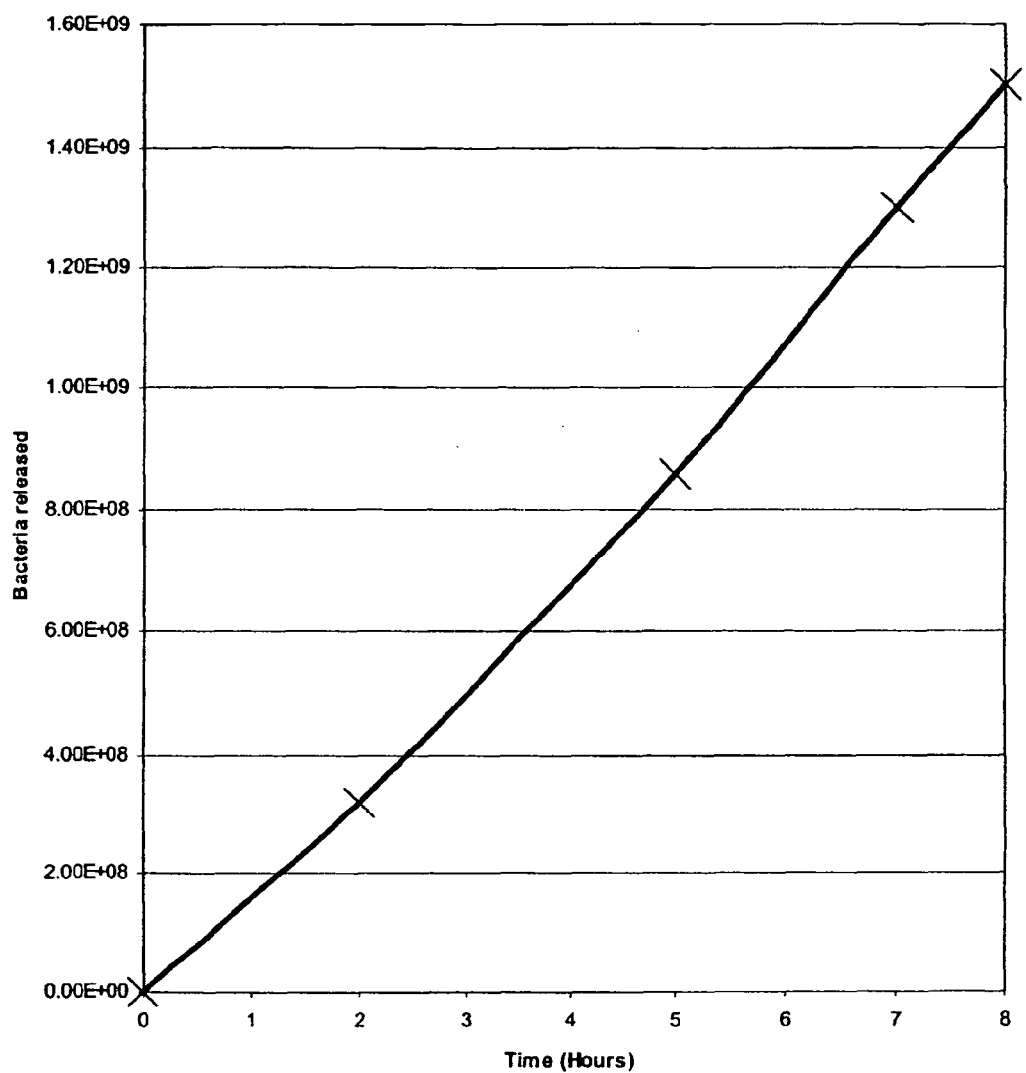
FIG. 7 shows the controlled release of beneficial microorganisms over an extended duration of 8 hours from the delivery system in its dosage form of monolithic tablets.

As depicted in FIG. 7, the results of this example demonstrate the capacity for the controlled release of BC over an extended duration, for example, from zero to eight hours. The rate of controlled release is linear from zero until approximately 8 hours.

Example 8

A delivery system in its dosage form as a monolithic tablet of approximately 532 mg containing a hydrophilic agent, an electrolytic agent, a release-modifying agent, an inert filler, and a BC was prepared as shown in Table 8. The hydrophilic agent employed is HPMC or PEO. The electrolytic agent used is $NaHCO_3$. The release-modifying agent employed is pectin, and the inert filler employed is MCC. The BC employed in this example consists of the bifidobacterium pre-blend of lyophilized powder and starch. Stearic acid is included as a flow agent, and silica is employed as a flow agent and desiccant. Turmeric is included as a colorant.

Figure 8:
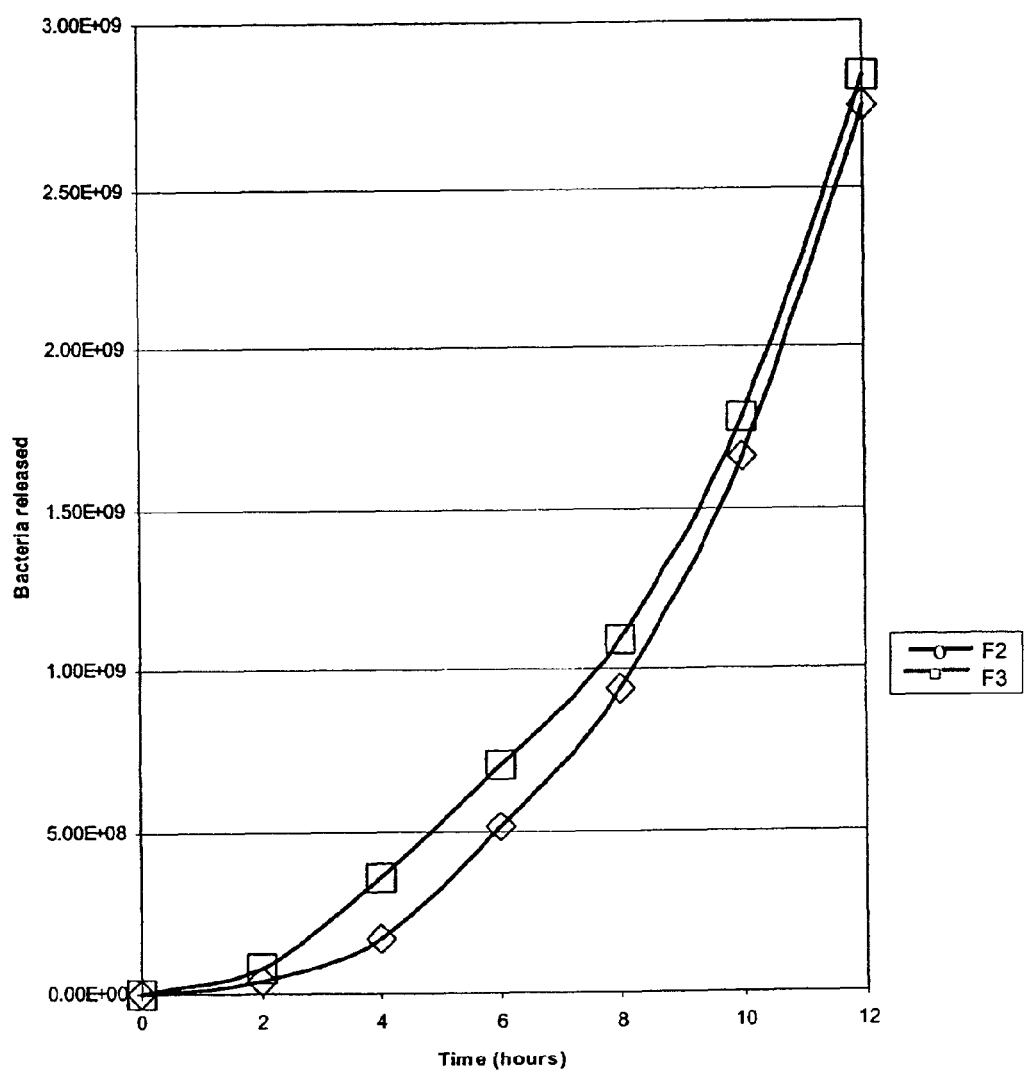
FIG. 8 shows the controlled release of beneficial microorganisms specific to the lower intestinal tract over an extended duration of 12 hours from the delivery system in its dosage form as monolithic tablets.

As depicted in FIG. 8, the results of this example demonstrate the capacity for the controlled release of BCs over an extended duration. The controlled release of the hydrophilic matrix is also shown to release in a profile favorable for the delivery of the BC, in this case consisting of bifidobacterium, after eight hours. Such an example would be useful for delivering the bifidobacterium to the lower intestine and beyond the lower intestine.

TABLE 8

| | Dosage Formulas (mg) | |
| --- | --- | --- |
| | F2 | F3 |
| *Bifidobacterium* bacteria pre-blend | 150 | 150 |
| HPMC | 150 | 0 |
| PEO | 0 | 150 |
| Pectin | 100 | 100 |
| NaHCO$_3$ | 100 | 100 |
| Stearic Acid | 16 | 16 |
| Silica | 16 | 16 |
| TOTAL WEIGHT | 532 | 532 |

Example 9

A delivery system in its dosage form as two-piece capsules of approximately 665 mg containing two hydrophilic agents, an electrolytic agent, a release-modifying agent, and a BC was prepared as shown in Table 9. The group G1 is the control. The hydrophilic agents employed are HPMC and Guar. The electrolytic agent employed is NaHCO$_3$. The release-modifying agent employed is pectin. The BC employed in this example consists of the lactic acid bacteria pre-blend of lyophilized powder and starch. Stearic acid is included as a flow agent, and silica is employed as a flow agent and desiccant.

Figure 9:
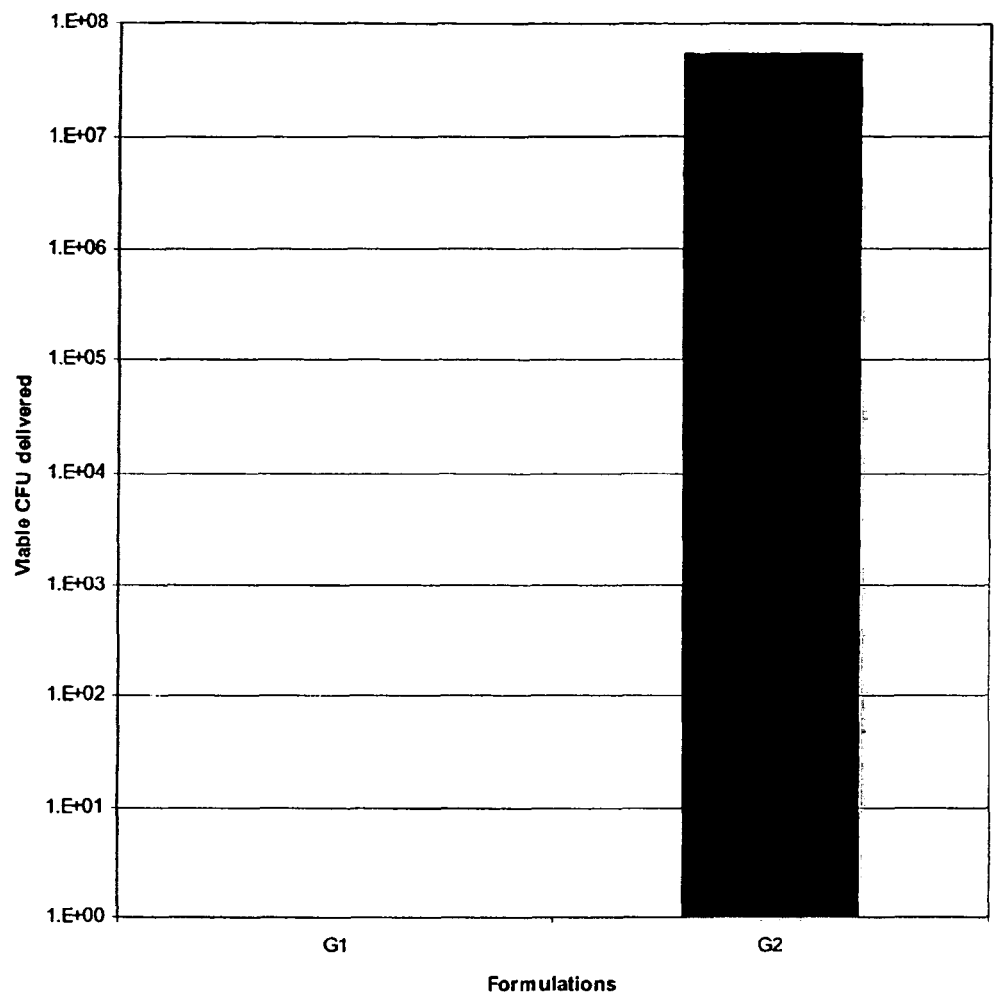
FIG. 9 shows the effects of a hydrophilic matrix on the controlled release of viable beneficial microorganisms into the small intestine from the delivery system in its dosage form as capsules.

The results of this example, as depicted in FIG. 9, demonstrate that the combination of the hydrophilic agents, the electrolytic agent, and the release-modifying agent is capable of controlling the release of the BC from its dosage form as a capsule. Dosage form flexibility, such as formulation of a tablet or a capsule, provides substantial adaptability during the manufacturing process.

TABLE 9

| | Dosage Formulas (mg) | |
| --- | --- | --- |
| | G1 (CTRL) | G2 |
| Lactic acid bacteria pre-blend | 150 | 150 |
| Pectin | 0 | 75 |
| HPMC | 0 | 110 |
| NaHCO$_3$ | 0 | 110 |
| Guar | 0 | 200 |
| Stearic Acid | 10 | 10 |
| Silica | 10 | 10 |
| TOTAL WEIGHT | 170 | 665 |

Example 10

A delivery system in its dosage form as monolithic tablets of approximately 684 mg and 342 mg containing a hydrophilic agent, an electrolytic agent, a release-modifying agent, an inert filler, and a BC was prepared as shown in Table 10. The hydrophilic agent employed is HPMC. The electrolytic agent employed is NaHCO$_3$. The release-modifying agent employed is pectin. The inert filler employed is the MCC. The BC employed in this example consists of the lactic acid bacteria pre-blend of lyophilized powder and starch. Stearic acid is included as a flow agent, and silica is employed as a flow agent and desiccant.

Figure 10:
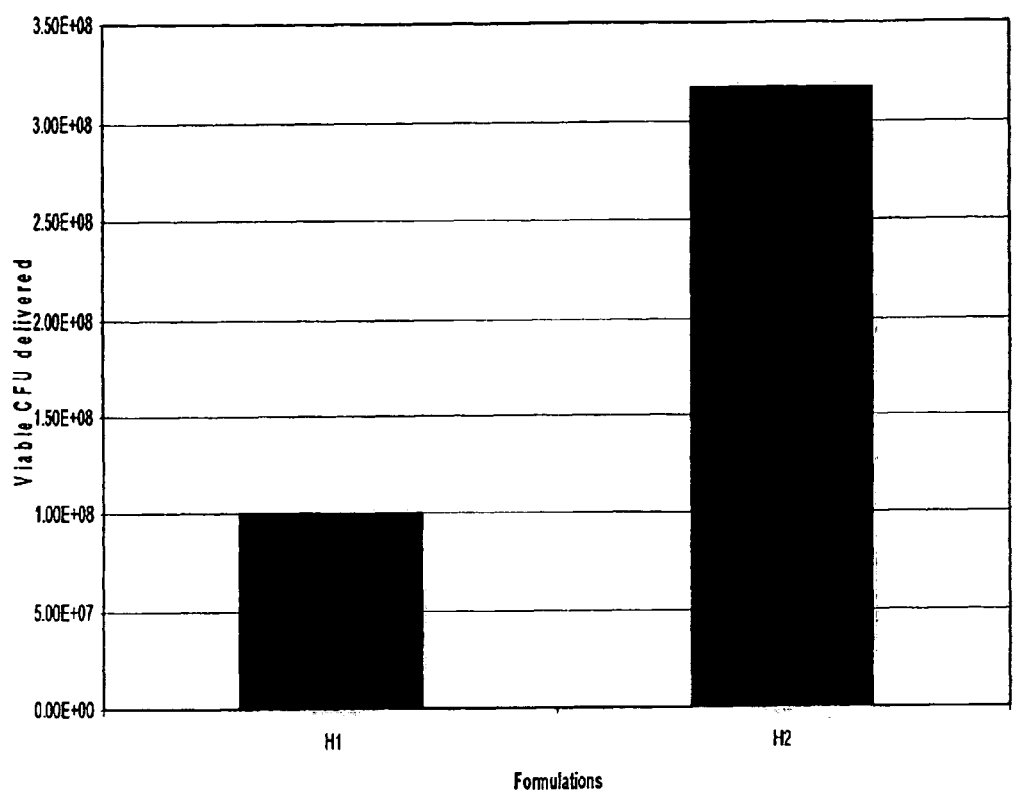
FIG. 10 shows the capacity for controlling geometric scalability, tablet size and shape variation in the present invention and the effect of such changes on the controlled release of viable beneficial microorganisms into the small intestine from the delivery system in its dosage form as monolithic tablets.

The results of this example, as depicted in FIG. 10, demonstrate that the combination of the hydrophilic agent, the electrolytic agent, and the release-modifying agent is capable of controlling geometric scalability, tablet shape, size and volume while controlling the release of the BC from the delivery system in its hydrophilic matrix and dosage form of a monolithic tablet. This flexibility of varying the dosage form is especially useful in manufacturing when differing formulation volumes is required, particularly altering tablet shapes and sizes.

TABLE 10

| | Dosage Formulas (mg) | |
| --- | --- | --- |
| | H1 | H2 |
| Lactic acid bacteria pre-blend | 75 | 150 |
| Pectin | 50 | 100 |
| HPMC | 50 | 100 |
| NaHCO$_3$ | 50 | 100 |
| Guar | 100 | 200 |
| Stearic Acid | 8 | 16 |
| Silica | 8 | 16 |
| Turmeric | 1 | 2 |
| TOTAL WEIGHT | 342 | 684 |

Example 11

A delivery system in its dosage form as monolithic tablets of approximately 684 mg containing a hydrophilic agent, an electrolytic agent, a release-modifying agent, an inert filler, and a BC was prepared as shown in Table 11. The hydrophilic agent employed is HPMC. The electrolytic agent used is NaHCO$_3$. The release-modifying agent employed is pectin, and the inert filler employed is the MCC. The BC employed in this example consists of the lactic acid bacteria pre-blend of lyophilized powder and starch. Stearic acid is included as a flow agent, and silica is employed as a flow agent and desiccant. Turmeric is included as a colorant.

Figure 11:
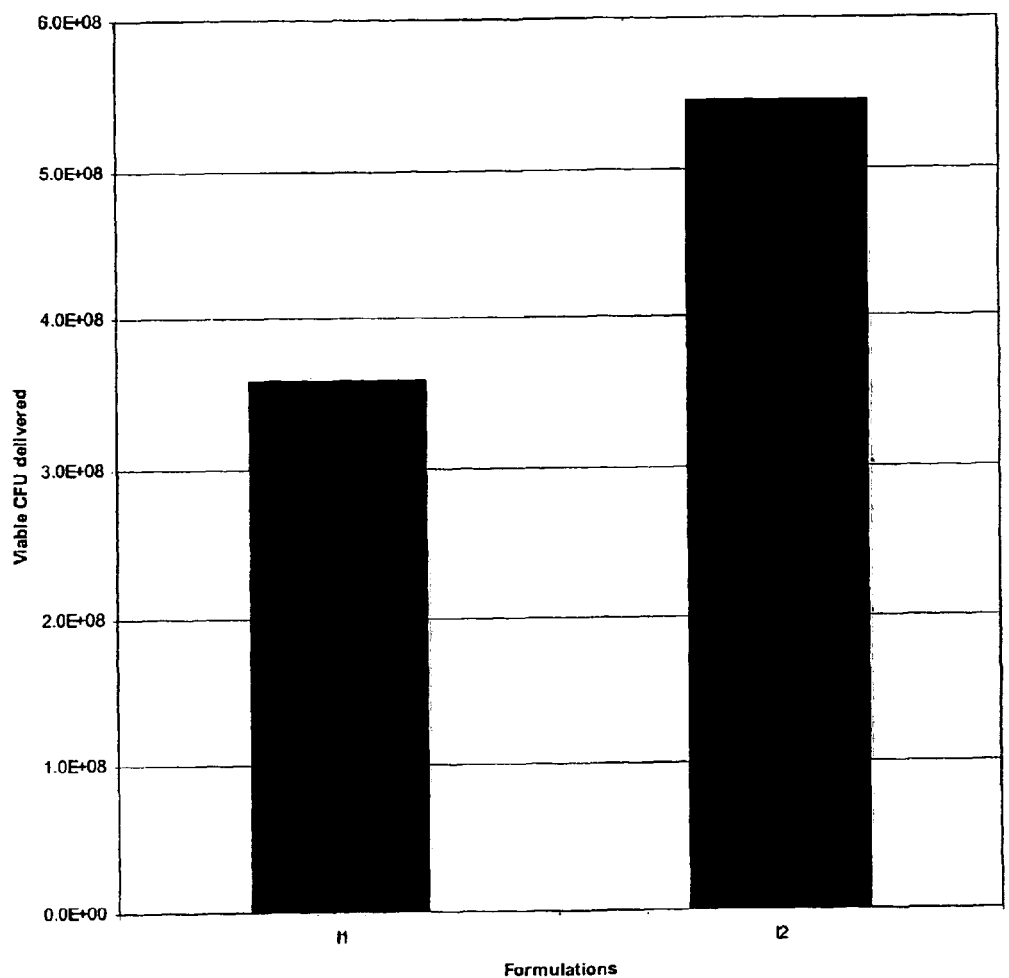
FIG. 11 shows the effects of drying the agents prior to tableting the controlled release of viable beneficial microorganisms into the small intestine from the delivery system in its dosage form as monolithic tablets.

The results of this example, as depicted in FIG. 11, demonstrate the application of drying an identical formulation of excipients of a pre-blend before tableting (I2) vs. a non-dried pre-blend (I1). The beneficial effects of drying are evidenced by the increase in viable lactic acid bacteria or probiotic CFU delivered in the dried pre-blend, I2, when compared to the non-dried pre-blend, I1.

TABLE 11

| | Dosage Formulas (mg) | |
| --- | --- | --- |
| | I1 | I2 |
| Lactic acid bacteria pre-blend | 150 | 150 |
| HPMC | 100 | 100 |
| Pectin | 100 | 100 |
| NAH(CO3)2 | 100 | 100 |
| MCC | 200 | 200 |
| Stearic Acid | 8 | 8 |
| Silica | 8 | 8 |
| Turmeric | 2 | 2 |
| TOTAL WEIGHT | 684 | 684 |

Example 12

A delivery system in its dosage form as a monolithic tablet of approximately 532 mg containing a hydrophilic agent, an electrolytic agent, a release-modifying agent, an inert filler, and a BC was prepared as shown in Table 12. The hydrophilic agent employed is HPMC of viscosity 4000 mPa (H1) or 15000 mPa (H2). The electrolytic agent employed is NaHCO₃. The release-modifying agent employed is pectin, and the inert filler employed is MCC. The BC employed in this example consists of the bifidobacterium pre-blend of lyophilized powder and starch. Stearic acid is included as a flow agent, and silica is employed as a flow agent and desiccant. Tumeric is included as a colorant.

Figure 12:
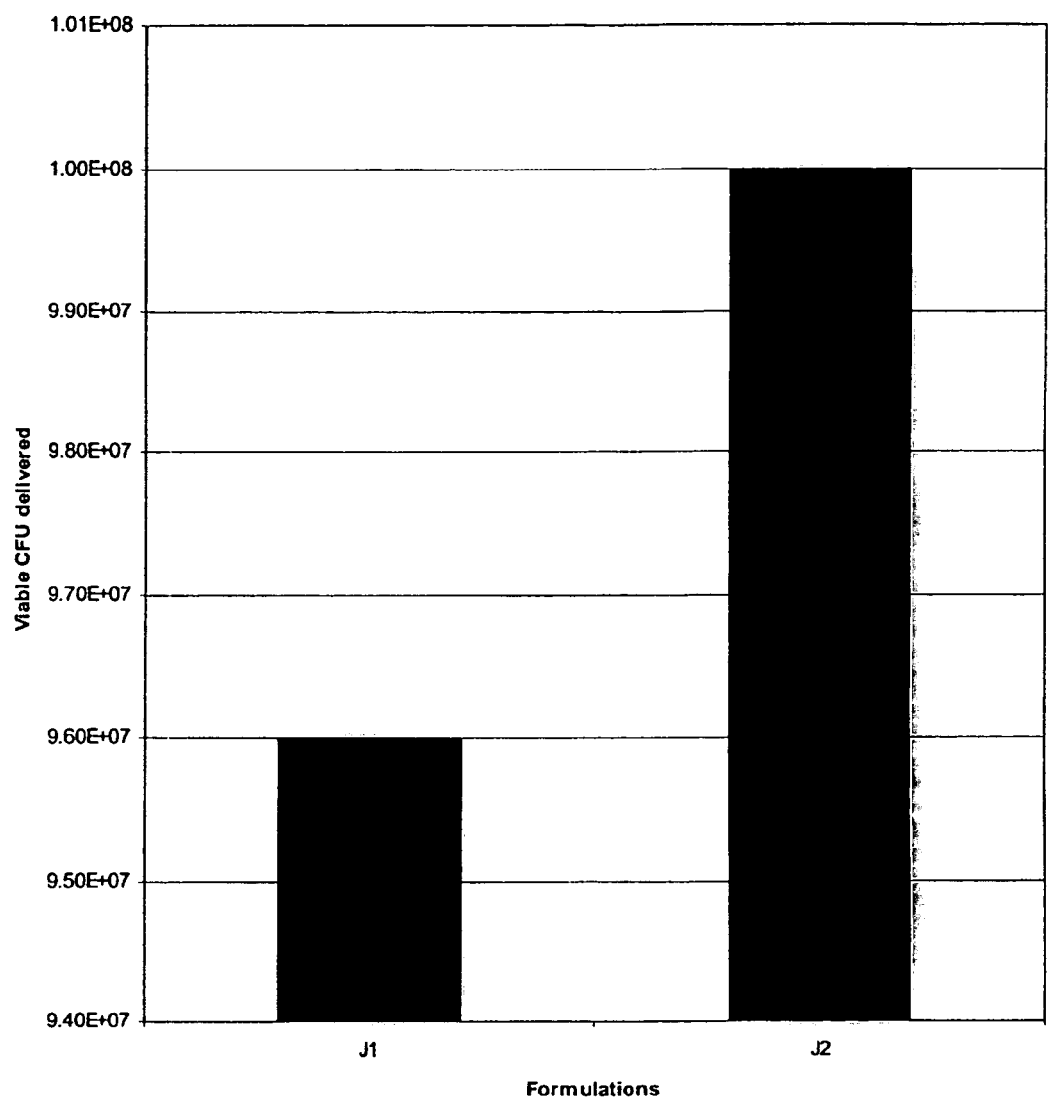
FIG. 12 shows the effects of a hydrophilic matrix employing hydrophilic agents of differing viscosities on the controlled release of viable beneficial microorganisms into the small intestine from the delivery system in its dosage form as capsules.

As depicted in FIG. 12, the results of this example demonstrate the capacity for differentially controlled release of viable BCs by employing hydrophilic agents of differing viscosities.

TABLE 12

|  | Dosage Formulas (mg) | |
| --- | --- | --- |
|  | H1 | H2 |
| Lactic acid bacteria pre-blend | 75 | 75 |
| HPMC, 4000 mPa | 50 | 0 |
| HPMC, 15000 mPa | 0 | 50 |
| Pectin | 50 | 50 |
| NaHCO₃ | 50 | 50 |
| MCC | 100 | 100 |
| Stearic Acid | 8 | 8 |
| Silica | 8 | 8 |
| Turmeric | 1 | 1 |
| TOTAL WEIGHT | 342 | 342 |

Example 13

A delivery system in its dosage form as a monolithic tablet of approximately 343 mg containing a hydrophilic agent, an electrolytic agent, a release-modifying agent, an inert filler, and a BC was prepared as shown in Table 13. The hydrophilic agent employed is HPMC. The electrolytic agent employed is NaHCO₃. The release-modifying agent employed is pectin, and the inert filler employed is MCC. The BC employed in this example consists of the lactic acid pre-blend of lyophilized powder and starch. Stearic acid is included as a flow agent, and silica is employed as a flow agent and desiccant. Tumeric is included as a colorant.

As depicted in FIG. 13, the results of this example demonstrate the capacity for increased stability over time when stored in an ambient environment (25 degrees C., 60% Relative Humidity), evidenced by a relatively constant amount of viable lactic acid bacteria CFU.

TABLE 13

|  | Dosage Formulas (mg) K1 |
| --- | --- |
| Lactic acid bacteria pre-blend | 75 |
| HPMC | 50 |
| Pectin | 50 |
| NaHCO₃ | 50 |
| MCC | 100 |
| Stearic Acid | 8 |
| Silica | 8 |
| Turmeric | 2 |
| TOTAL WEIGHT | 343 |

The discussion above is descriptive, illustrative and exemplary and is not to be taken as limiting the scope defined by any appended claims.

The invention claimed is:

1. A controlled release formulation for oral delivery to an intestinal system, the formulation comprising:
    about 5% to 40% by total weight of hydroxypropyl methylcellulose;
    about 5% to 40% by total weight of pectin;
    about 1% to 40% by total weight of at least one electrolytic agent selected from the group consisting of sodium carbonate and sodium bicarbonate; and
    a probiotic.

2. The controlled release formulation of claim 1 wherein the hydroxypropyl methylcellulose and the pectin are present in a ratio of about 1:1.

3. The controlled release formulation of claim 1 having a total weight of approximately 343 mg and consisting of the following components, each in the approximate amount of:
    50 mg of hydroxypropyl methylcellulose;
    50 mg of pectin;
    50 mg of sodium bicarbonate;
    100 mg of microcrystalline cellulose;
    8 mg of stearic acid;
    8 mg of silica;
    2 mg of a turmeric; and
    75 mg of a lactic acid bacteria pre-blend comprising a lyophilized powder including the probiotic and starch.

4. The controlled release formulation of claim 1 wherein the probiotic is non-viable.

5. The controlled release formulation of claim 1 having a total weight of approximately 532 mg and consisting of the following components, each in the approximate amount of:
    150 mg of hydroxypropyl methylcellulose;
    100 mg of pectin;
    100 mg of sodium bicarbonate;
    16 mg of stearic acid;
    16 mg of silica; and
    150 mg of a bifidobacterium bacteria pre-blend comprising a lyophilized powder including the probiotic and starch.

6. The formulation of claim 1 wherein the probiotic is a lactic acid bacteria.

7. The formulation of claim 1 wherein the probiotic comprises one or more of *Lactobacillus acidophilus, Lactobacillus rhamnosus, Lactobacillus salivarius, Lactobacillus plantarum, Streptococcus thermophilus, Bifidobacterium infantis, Bifidobacterium bifidum*, or *Bifidobacterium longum*.

8. The formulation of claim 1 wherein the electrolytic agent is sodium bicarbonate.

9. The formulation of claim 1 wherein said formulation is a directly compressed monolithic tablet.

10. A controlled release formulation for oral delivery to an intestinal system, the formulation comprising:
    about 5% to 40% by total weight of hydroxypropyl methylcellulose;
    about 5% to 40% by total weight of pectin;
    about 1% to 40% by total weight of sodium bicarbonate; and
    a probiotic;
    wherein said formulation is a monolithic tablet without an enteric coating.

11. The controlled release formulation of claim 10 wherein the hydroxypropyl methylcellulose and the pectin are present in a ratio of about 1:1.

12. The controlled release formulation of claim 10 having a total weight of approximately 343 mg and consisting of the following components, each in the approximate amount of:
  50 mg of hydroxypropyl methylcellulose;
  50 mg of pectin;
  50 mg of sodium bicarbonate;
  100 mg of microcrystalline cellulose;
  8 mg of stearic acid;
  8 mg of silica;
  2 mg of a turmeric; and
  75 mg of a lactic acid bacteria pre-blend comprising a lyophilized powder including the probiotic and starch.

13. The controlled release formulation of claim 10 wherein the probiotic is non-viable.

14. The controlled release formulation of claim 10 having a total weight of approximately 532 mg and consisting of the following components, each in the approximate amount of:
  150 mg of hydroxypropyl methylcellulose;
  100 mg of pectin;
  100 mg of sodium carbonate bicarbonate;
  16 mg of stearic acid;
  16 mg of silica; and
  150 mg of a bifidobacterium bacteria pre-blend comprising a lyophilized powder including the probiotic and starch.

15. The formulation of claim 10 wherein the probiotic is a lactic acid bacteria.

16. The formulation of claim 10 wherein the probiotic comprises one or more of *Lactobacillus acidophilus, Lactobacillus rhamnosus, Lactobacillus salivarius, Lactobacillus plantarum, Streptococcus thermophilus, Bifidobacterium infantis, Bifidobacterium bifidum*, or *Bifidobacterium longum*.

17. The formulation of claim 10 wherein said formulation is a directly compressed monolithic tablet.

18. A controlled release formulation for oral delivery to an intestinal system, the formulation comprising:
  about 5% to 40% by total weight of hydroxypropyl methylcellulose;
  about 5% to 40% by total weight of pectin;
  about 1% to 40% by total weight of sodium carbonate; and
  a probiotic;
  wherein said formulation is a monolithic tablet without an enteric coating.

* * * * *